US012599509B2

(12) United States Patent
Komatsubara et al.

(10) Patent No.: US 12,599,509 B2
(45) Date of Patent: Apr. 14, 2026

(54) CAT DIAPER

(71) Applicant: UNICHARM CORPORATION, Ehime (JP)

(72) Inventors: Daisuke Komatsubara, Kanonji (JP); Yumi Matsumoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 905 days.

(21) Appl. No.: 17/752,250

(22) Filed: May 24, 2022

(65) Prior Publication Data

US 2022/0280355 A1 Sep. 8, 2022

Related U.S. Application Data

(63) Continuation of application No. PCT/JP2020/038734, filed on Oct. 14, 2020.

(30) Foreign Application Priority Data

Nov. 25, 2019 (JP) ................................. 2019-212723
Nov. 25, 2019 (JP) ................................. 2019-212729

(51) Int. Cl.
*A61F 13/494* (2006.01)
*A01K 23/00* (2006.01)
(Continued)

(52) U.S. Cl.
CPC ........ *A61F 13/49413* (2013.01); *A01K 23/00* (2013.01); *A61F 13/531* (2013.01);
(Continued)

(58) Field of Classification Search
CPC .. A61F 13/15; A61F 13/49413; A61F 13/531; A61F 13/5638; A61F 2013/15186;
(Continued)

(56) References Cited

U.S. PATENT DOCUMENTS 7,195,618 B2    3/2007  Ikegami
9,332,731 B2    5/2016  Komatsubara et al.
(Continued)

FOREIGN PATENT DOCUMENTS

CN        104883878 A       9/2015
JP        2012-205542 A     10/2012
(Continued)

OTHER PUBLICATIONS

International Search Report issued in corresponding International Application No. PCT/JP2020/038734 mailed Jan. 12, 2021 (5 pages).

(Continued)

*Primary Examiner* — Michele Kidwell
(74) *Attorney, Agent, or Firm* — Osha Bergman Watanabe & Burton LLP

(57) ABSTRACT

A cat diaper has a lateral direction along a waistline of a cat and a longitudinal direction orthogonal to the lateral direction, and includes: a body portion that includes an absorbent core, and has a stomach region, a crotch region, and a back region, and a fastening tape that extends from each side of the body portion in the lateral direction, and joins the stomach region and the back region, the absorbent core having a constricted portion that tapers toward an inner side of the absorbent core in the lateral direction, and a stomach-side end of an innermost edge of the constricted portion in the lateral direction being positioned between a center of the absorbent core in the longitudinal direction and a back side of the cat diaper.

9 Claims, 7 Drawing Sheets

(51) Int. Cl.
    *A61F 13/15*        (2006.01)
    *A61F 13/531*     (2006.01)
    *A61F 13/56*      (2006.01)

(52) U.S. Cl.
    CPC ..................... *A61F 13/5638* (2013.01); *A61F 2013/15186* (2013.01); *A61F 2013/5315* (2013.01)

(58) Field of Classification Search
    CPC .. A61F 2013/5315; A61F 23/00; A01K 23/00
    See application file for complete search history.

(56) References Cited

U.S. PATENT DOCUMENTS

| | | | | |
|---|---|---|---|---|
| 2005/0154267 | A1* | 7/2005 | Bardy ................... | G16H 50/30 |
| | | | | 128/920 |
| 2014/0076246 | A1* | 3/2014 | Komatsubara ......... | A01K 23/00 |
| | | | | 119/869 |
| 2015/0305306 | A1 | 10/2015 | Komatsubara | |
| 2015/0327516 | A1* | 11/2015 | Komatsubara ......... | A01K 23/00 |
| | | | | 119/869 |
| 2016/0008183 | A1* | 1/2016 | Komatsubara ......... | A01K 23/00 |
| | | | | 604/385.09 |
| 2017/0280684 | A1* | 10/2017 | Komatsubara ......... | A01K 23/00 |
| 2019/0060136 | A1 | 2/2019 | Turner et al. | |
| 2022/0279758 | A1* | 9/2022 | Komatsubara ......... | A01K 23/00 |
| 2022/0409444 | A1* | 12/2022 | Komatsubara ........ | A61F 13/494 |
| 2024/0325217 | A1* | 10/2024 | Komatsubara ........ | A61F 13/496 |
| 2025/0008927 | A1* | 1/2025 | Koido ................... | A61F 13/493 |

FOREIGN PATENT DOCUMENTS

| | | |
|---|---|---|
| JP | 3180238 U | 12/2012 |
| JP | 2013-135638 A | 7/2013 |
| JP | 2017-131160 A | 8/2017 |
| KR | 10-2005-0050551 A | 5/2005 |
| WO | 2012/132886 A1 | 10/2012 |

OTHER PUBLICATIONS

Written Opinion issued in corresponding International Application No. PCT/JP2020/038734 mailed Jan. 12, 2021 (3 pages).

Office Action issued in corresponding Indonesian Patent Application No. P00202205822, dated Dec. 14, 2023 (6 pages).

Office Action issued in corresponding Taiwanese Patent Application No. 109137196, dated Jan. 25, 2024 (6 pages).

Office Action issued in corresponding Chinese Patent Application No. 202080078715.2, dated Jan. 31, 2023, with translation (16 pages).

Office Action issued in corresponding Korean Application No. 10-2022-7016131 mailed Aug. 22, 2025 (23 pages).

Office Action issued in corresponding Malaysian Application No. PI2022002321 mailed Oct. 8, 2025 (4 pages).

* cited by examiner

CAT DIAPER

CROSS-REFERENCE TO RELATED APPLICATIONS

The present application claims priority to Japanese Patent Application Nos. 2019-212723 filed on Nov. 25, 2019, and 2019-212729 filed on Nov. 25, 2019, which are incorporated herein by reference and are regarded as a part of the description of this specification.

BACKGROUND

Technical Field

The present invention relates to a cat diaper to be put on a cat.

Description of Related Art

Patent Literature 1 discloses a pet diaper. The pet diaper of Patent Literature 1 includes a belly pad portion brought into contact with the belly side of a pet, a back pad portion brought into contact with the back side of the pet, a tail hole which is provided in the back pad portion and through which the tail passes, and a fastener tape provided in the belly pad portion. When the pet diaper of Patent Literature 1 is put on a pet, the tail hole is slipped over the tail, the belly pad portion is brought into contact with the belly side of the pet, the back pad portion is brought into contact with the back side, and the fastener tape is fastened to the back pad portion (see FIG. 4 of Patent Literature 1).

PATENT LITERATURE

Patent Literature 1: Japanese Unexamined Patent Application Publication No. 2017-131160

The pet diaper disclosed in Patent Literature 1 is constituted so that it can be put on dogs and cats. In addition, as a result of extensive investigation, the applicant has found that there is a big difference in the normal way of body movement between cats and dogs. Specifically, it has been found that, in many cases, while dogs tend to perform movement in a planar direction, such as running on the ground, cats tend to perform movement in a vertical direction, such as jumping up and down, unlike dogs. When trying to move its body in a vertical direction, a cat bends back legs and then instantly stretches them, or stretches the stomach or back that has been pulled in or hunched, as soon as it bends and stretches legs. Therefore, the skin around the stomach, the buttocks, and the legs are likely to stretch and contract much. Therefore, as time passes since the cat has worn the diaper, an inconvenient condition in that the diaper is displaced or detached occurs.

SUMMARY

An aspect of the present invention provides a cat diaper that can be inhibited from being displaced while being worn.

A cat diaper according to another aspect has a lateral direction that is arranged along a waistline direction of a cat and a longitudinal direction that is orthogonal to the lateral direction and extends in a direction connecting a stomach side and a back side of the cat, the cat diaper comprising a body portion that has an absorbent core and straddles a stomach-side region (or a stomach region), a crotch region, and a back-side region (or a back region), and a fastening tape that extends to two outer sides (or both outsides of the body portion) in the lateral direction from the body portion and joins the stomach-side region and the back-side region. The absorbent core has a constricted portion that tapers toward an inner side in the lateral direction. A stomach-side end edge (or a stomach-side end) at an inner edge (or an innermost edge) of the constricted portion in the lateral direction is positioned away from a center of the absorbent core in the longitudinal direction toward the back side (positioned between the center of the absorbent core in the longitudinal direction and the back side). Hereinafter, the phrasing "away from . . . toward" means "between."

A cat diaper according to another aspect has a lateral direction that is arranged along a waistline direction of a cat and a longitudinal direction that is orthogonal to the lateral direction and extends in a direction connecting a stomach side and a back side of a pet, the cat diaper comprising a body portion that has an absorbent core and straddles a stomach-side region, a crotch region, and a back-side region, leg opening portions that are arranged around (or respectively correspond to) the cat's legs, and a fastening tape that extends to two outer sides (or both outsides of the body portion) in the lateral direction from the body portion and joins the stomach-side region and the back-side region. Each of the leg opening portions has a stomach-side edge (or a stomach-side opening edge) that extends to an inner side in the lateral direction from an outer edge (or a lateral outer edge) of the body portion on the stomach side, a back-side edge (or a back-side opening edge) that extends to an inner side in the lateral direction from the outer edge of the body portion on the back side, and a longitudinal edge (or a longitudinal opening edge) that connects the stomach-side edge and the back-side edge and extends in the longitudinal direction. In a case where a represents a length of the stomach-side edge in the longitudinal direction, and b represents a length of the stomach-side edge in the lateral direction, $a < b$ is satisfied.

A cat diaper according to still another aspect has a lateral direction that is arranged along a waistline direction of a cat and a longitudinal direction that is orthogonal to the lateral direction and extends in a direction connecting a stomach side and a back side of a pet, the cat diaper comprising a body portion that has an absorbent core and straddles a stomach-side region, a crotch region, and a back-side region, leg opening portions that are arranged around (or respectively correspond to) the cat's legs, and a fastening tape that extends to two outer sides (or both outsides of the body portion) in the lateral direction from the body portion and joins the stomach-side region and the back-side region. Each of the leg opening portions has a stomach-side edge that extends to an inner side in the lateral direction from an outer edge of the body portion on the stomach side, a back-side edge that extends to an inner side in the lateral direction from an outer edge of the body portion on the back side, and a longitudinal edge that connects the stomach-side edge and the back-side edge and extends in the longitudinal direction. In a case where c represents a distance between the fastening tape and the longitudinal edge in the longitudinal direction, and b represents a length of the stomach-side edge in the lateral direction, $c < b$ is satisfied.

DETAILED DESCRIPTION

(1) Summary of Embodiments

Figure 1:
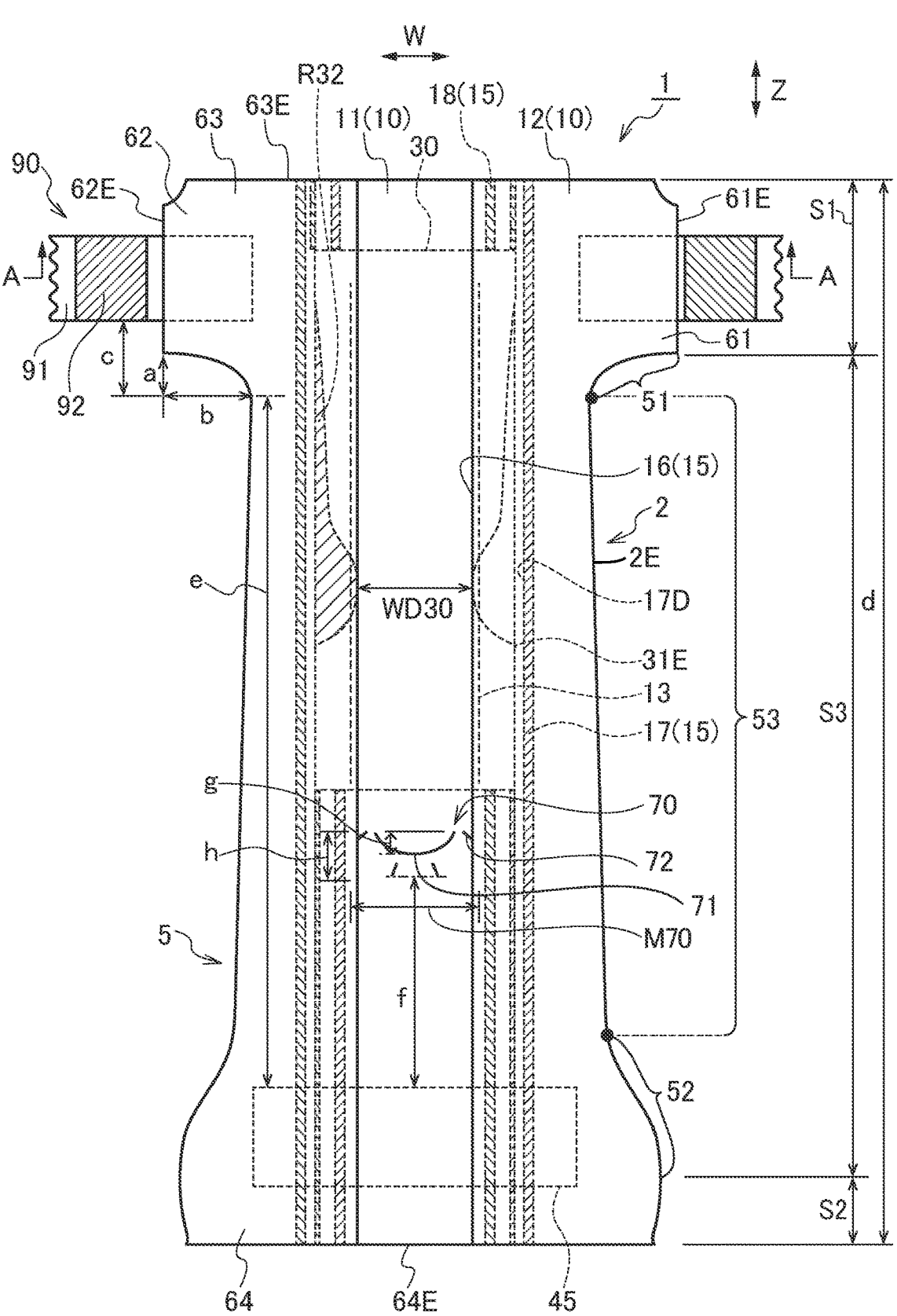
FIG. 1 is a plan view of a cat diaper according to one or more embodiments, seen from a skin surface side.

At least following matters will become clear with description of this specification and attached drawings.

A cat diaper of one or more embodiments has a lateral direction that is arranged along a waistline direction of a cat and a longitudinal direction that is orthogonal to the lateral direction and extends in a direction connecting a stomach side and a back side of the cat, the cat diaper comprising a body portion that has an absorbent core and straddles a stomach-side region, a crotch region, and a back-side region, and a fastening tape that extends to two outer sides in the lateral direction from the body portion and joins the stomach-side region and the back-side region. The absorbent core has a constricted portion that tapers toward an inner side in the lateral direction. A stomach-side end edge at an inner edge (or an innermost edge) of the constricted portion in the lateral direction is positioned away from a center of the absorbent core in the longitudinal direction toward the back side. As a result of observing the cat in the diaper, the applicant has found that the length of the absorbent core, which extends toward the stomach side from the position where a leg width of is the smallest, in the longitudinal direction corresponds to the length of the absorbent core, which extends toward the stomach side from the stomach-side end edge, in the longitudinal direction. Because the absorbent core that extends toward the stomach side from the portion where the leg width is the smallest can be long enough in the longitudinal direction, even in a case where the cat repeatedly moves its legs back and forth when moving in a vertical direction, the cat's body can be kept covered with the absorbent core. Furthermore, because the absorbent core that extends toward the stomach side from the position where the leg width is the smallest can be long enough in the longitudinal direction, even in a case where the skin on the stomach stretches and contracts much, the absorbent core can keep conforming to the movement, which makes it easy for the cat to keep on wearing the diaper.

According to one or more embodiments, the constricted portion may have a side edge that connects a front end edge (or a front end) positioned on the stomach side, a back end edge (or a back end) positioned on the back side, and the inner edge, and a distance between a first intersection point where a virtual line that passes through a center of the constricted portion in the lateral direction and extends in the longitudinal direction intersects with a stomach-side edge that extends to the inner edge from the front end edge and a second intersection point where the virtual line intersects with a back-side edge that extends to the inner edge from the back end edge may be less than 40% of a length of the absorbent core in the longitudinal direction. When the cat moves in the vertical direction, due to the impact of landing or the like or the stretching or contraction of the skin in the longitudinal direction, the diaper is easily displaced in the longitudinal direction. At this time, the amount of displacement of the diaper around the back legs in the longitudinal direction is likely to be limited to not more than 40% of the absorbent core. For example, even in a case where the force that makes the diaper displaced in the longitudinal direction due to impact or the like acts, the cat's body can be kept covered with the diaper.

According to one or more embodiments, a distance between a front outer end edge (or a front outer edge) of the absorbent core positioned on the stomach side and the first intersection point may be longer than a distance between a back outer end edge (or a back outer edge) of the absorbent core positioned on the back side and the second intersection point. The first intersection point and the second intersection point are positioned at the center of the constricted portion in the lateral direction, and are likely to come into contact with the center of the back leg in the lateral direction. The length of the absorbent core, which extends toward the stomach side from the center of the constricted portion in the lateral direction, in the longitudinal direction is greater than the length of the absorbent core, which extends toward the back side from the center of the constricted portion in the lateral direction, in the longitudinal direction. Because the absorbent core that extends toward the stomach side from the back leg can be long enough in the longitudinal direction, even in a case where the skin on the stomach stretches and contracts much, the absorbent core can keep conforming to the movement, which makes it easy for the cat to keep on wearing the diaper.

According to one or more embodiments, the absorbent core may have a stomach-side region (or a stomach core region) that is positioned away from the center of the absorbent core in the longitudinal direction toward the stomach side and a back-side region (or a back core region) that is positioned away from the center of the absorbent core in the longitudinal direction toward the back side, and an area of the stomach-side region may be larger than an area of the back-side region. The urination opening of a female dog is likely to come into contact with the back-side region, while the urination opening of a male dog is likely to come into contact with the stomach-side region. On the other hand, the urination opening of both the male and female cats is likely to come into contact with the back-side region. In a case where the area of the stomach-side region in the cat diaper is increased, the diaper can retain the body fluid that diffuses to the stomach-side region from the back-side region. Drinking small amounts of water in general, cats are susceptible to urinary diseases. The cats with urinary diseases often show the symptoms of polydipsia and polyuria. The cats with polyuria have a higher tendency to pass urine that spreads in the stomach-side region of the absorbent core. Increasing the area of the stomach-side region makes it possible for the diaper to retain the body fluid diffusing to the stomach-side region from the back-side region even in a case where the cat has polyuria.

According to one or more embodiments, the absorbent core may have a stomach-side region (or a stomach core region) that is positioned away from the center of the absorbent core in the longitudinal direction toward the stomach side and a back-side region (or a back core region) that is positioned away from the center of the absorbent core in the longitudinal direction toward the back side, a length of the absorbent core in the lateral direction at the inner edge of the constricted portion may be not more than 50% of the maximum length of the absorbent core in the lateral direction within the back-side region. The difference between the maximum length of the absorbent core in the lateral direction within the back-side region and the width of the absorbent core at the inner edge of the constricted portion can be made large. The urination opening of both the male and female cats is likely to come into contact with the back-side region. In the cat diaper, in a case where the maximum length of the absorbent core in the lateral direction within the back-side region is increased, the absorption capacity of the back-side region can be secured.

According to one or more embodiments, a tail hole may be formed in the body portion, and the maximum length of the tail hole in the lateral direction may be equal to or greater than the length of the absorbent core in the lateral direction at the inner edge of the constricted portion. When putting a diaper on a cat, a user inserts the cat's tail into the tail hole. As a result, the tail hole can be pulled in the lateral direction by the tail, and the force that stretches the tail hole in the lateral direction is applied to the absorbent core. The widening of the absorbent core in the lateral direction can suppress the wrinkling of the absorbent core, which makes it easy for the absorbent core to secure length in the lateral direction while the diaper is being worn. Because the maximum length of the tail in the lateral direction is equal to or greater than the length of the absorbent core of the constricted portion in the lateral direction, in a case where the force of widening the absorbent core acts on the entire tail hole in the lateral direction, the entire absorbent core in the constricted portion can widen in the lateral direction.

According to one or more embodiments, the cat diaper may have core wraps that cover a skin facing surface and a non-skin facing surface of the absorbent core, and a region overlapping with the constricted portion may be provided with an overlap portion where the core wraps overlap with each other. According to one or more embodiments, the stiffness of the overlap portion in the vicinity of the constricted portion can be increased. As a result, wrinkling of the constricted portion of the absorbent core can be suppressed, and the fit of the diaper can be maintained.

According to one or more embodiments, the cat diaper may have a rising leak-proof gather that is positioned to be closer to the skin side than the absorbent core, the leak-proof gather may have a rising portion that is capable of rising up and a fixed portion that is positioned away from the rising portion toward the outer side in the lateral direction and functions as a base point for the rising portion to rise up, and the inner edge of the fixed portion may be positioned away from the inner edge of the constricted portion toward the outer side in the lateral direction. In the leak-proof gather, the rising portion rises up from the fixed portion as a base point, and sometimes the rising portion and the entirety of the fixed portion rise up from the outer edge of the absorbent core as a base point due to the stiffness difference in the absorbent core. At this time, in the region where the constricted portion is provided, the inner edge of the fixed portion is positioned away from the inner edge of the constricted portion functioning as the outer edge of the absorbent core toward the outer side in the lateral direction. Accordingly, the rising portion and the entirety of the fixed portion rise up from the outer edge of the constricted portion as a base point. In the region where the constricted portion is provided, because the length of the absorbent core in the lateral direction is relatively small, there is a risk that the body fluid will be guided to the outer side of the absorbent core in the lateral direction. However, because the rising portion that rises up is high enough, leakage can be suppressed.

According to one or more embodiments, the length of the inner edge of the constricted portion in the longitudinal direction may be not more than 30% of the length of the absorbent core in the longitudinal direction. According to one or more embodiments, in a state where the diaper is fitted to the position where the leg width is the smallest, the amount of displacement of the diaper in the longitudinal direction is not more than 30% of the absorbent core. For example, even in a case where the force that makes the diaper displaced in the longitudinal direction due to impact or the like acts, the cat's body can be kept covered with the diaper.

A cat diaper of one or more embodiments has a lateral direction that is arranged along a waistline direction of a cat and a longitudinal direction that is orthogonal to the lateral direction and extends in a direction connecting a stomach side and a back side of a pet, the cat diaper comprising a body portion that has an absorbent core and straddles a stomach-side region, a crotch region, and a back-side region, leg opening portions that are arranged around the cat's legs, and a fastening tape that extends to two outer sides in the lateral direction from the body portion and joins the stomach-side region and the back-side region. Each of the leg opening portions has a stomach-side edge that extends to an inner side in the lateral direction from an outer edge of the body portion on the stomach side, a back-side edge that extends to an inner side in the lateral direction from an outer edge of the body portion on the back side, and a longitudinal edge that connects the stomach-side edge and the back-side edge and extends in the longitudinal direction. In a case where a represents a length of the stomach-side edge in the longitudinal direction, and b represents a length of the stomach-side edge in the lateral direction, a<b is satisfied. The leg opening portions are arranged so as to surround the back legs of the cat, and the stomach-side edge of each of the leg opening portions comes into contact with the stomach-side surface of the back leg of the cat. The length b of the stomach-side edge in the lateral direction is greater than the length a of the stomach-side edge in the longitudinal direction. Therefore, when the leg opening portions are fitted around the legs, a region can be secured which extends in the lateral direction in a range short in the longitudinal direction. Because the leg opening portions tighten some parts in the lateral direction within the range short in the longitudinal direction, it is easy to tightly fit the diaper around the legs. By tightly fitting the diaper around the legs, even for a cat which has relatively much flesh or has bent joints and thus not easy to tightly fit the diaper around the legs, a user can easily tightly fit the diaper around the legs without paying special attention, and the inconvenient condition that the diaper is detached while being worn can be suppressed.

A cat diaper of one or more embodiments has a lateral direction that is arranged along a waistline direction of a cat and a longitudinal direction that is orthogonal to the lateral direction and extends in a direction connecting a stomach side and a back side of a pet, the cat diaper comprising a body portion that has an absorbent core and straddles a stomach-side region, a crotch region, and a back-side region, leg opening portions that are arranged around the cat's legs, and a fastening tape that extends to two outer sides in the lateral direction from the body portion and joins the stomach-side region and the back-side region. Each of the leg opening portions has a stomach-side edge that extends to an inner side in the lateral direction from an outer edge of the body portion on the stomach side, a back-side edge that extends to an inner side in the lateral direction from an outer edge of the body portion on the back side, and a longitudinal edge that connects the stomach-side edge and the back-side edge and extends in the longitudinal direction. In a case where c represents a distance between the fastening tape and the longitudinal edge in the longitudinal direction, and b represents a length of the stomach-side edge in the lateral direction, c<b is satisfied. When the diaper is put on a cat, the fastening tape is pulled in the lateral direction and joined to a target portion or the like. At this time, the stomach-side edge of the leg opening portions is pulled in the lateral direction, and a line that starts from the portion between both the back legs, passes the back legs, and extends to the back side is configured with a line connecting the longitudinal edge and the fastening tape. Because the distance c is shorter than the length b of the stomach-side edge in the lateral direction, when the leg opening portions are fitted around the legs, a region can be secured which extends in the lateral direction within a short range in the longitudinal direction. Because the leg opening portions tighten some parts in the lateral direction within the range short in the longitudinal direction, it is easy to tightly fit the diaper around the legs. Tightly fitting the leg opening portions around the legs makes it possible to suppress the inconvenient condition in that the diaper is detached while being worn.

According to one or more embodiments, in a case where d represents a length of the body portion in the longitudinal direction, the ratio of a to d may be 10% or less. According to one or more embodiments, the ratio of the length a of the stomach-side edge in the longitudinal direction to the total length of the body portion of the diaper is low. Therefore, the diaper around the leg can be inhibited from being displaced in the longitudinal direction. As a result, the inconvenient condition in that the diaper is detached while being worn due to the increase in the amount of displacement in the longitudinal direction or the diaper hinders the cat from moving its legs back and forth can be suppressed.

According to one or more embodiments, the fastening tape may be arranged in the stomach-side region, at least a part of the target portion to which the fastening tape is to be fastened may be provided in the back-side region, and in a case where e represents a distance between the stomach-side edge and the target portion in the longitudinal direction and d represents a length of the body portion in the longitudinal direction, the ratio of e to d may be 60% or more. The distance e between the stomach-side edge and the target portion in the longitudinal direction is the length of a region that covers the body from the stomach side to the back side and is deformed in accordance with the body movement or the stretching and contraction of the skin in a state where the fastening tape is fastened to the target portion. Because the ratio of the length of the distance e between the stomach-side edge and the target portion in the longitudinal direction to the total length of the body portion of the diaper is high, a wide region deformed in accordance with the cat's movement can be secured.

According to one or more embodiments, a tail hole having a hole body portion (or a hole body) through which the cat's tail is capable of being inserted is provided in the body portion, the fastening tape may be arranged in the stomach-side region, at least a part of a target portion to which the fastening tape is to be fastened may be provided in the back-side region, and in a case where f represents a distance between a back-side end edge (or a back-side tail edge) of the tail hole and the target portion in the longitudinal direction and d represents a length of the body portion in the longitudinal direction, a ratio of f to d may be 20% or more. In a configuration having a notch portion (or a notch), the distance f is a distance between a region consisting of the notch portion and the hole body portion and the target portion. The distance f between the back-side end edge of the tail hole and the target portion in the longitudinal direction is the length of a region that covers a region from the tail hole to the back side and is deformed in accordance with the body movement or the stretching and contraction of the skin on the back side in a state where the fastening tape is fastened to the target portion. Because the ratio of the length f to the total length of the body portion is high, a wide region that is deformed in accordance with the cat's movement or the like can be secured on the back side, which allows the diaper to conform to the movement of the back side and makes it possible to inhibit the diaper from being displaced by accident.

According to one or more embodiments, a tail hole having a hole body portion through which a cat's tail is capable of being inserted may be provided in the body portion, the fastening tape may be arranged in the stomach-side region, at least a part of a target portion to which the fastening tape is to be fastened may be provided in the back-side region, and in a case where e represents a distance between the stomach-side edge and the target portion in the longitudinal direction and g represents a maximum length of the hole body portion in the longitudinal direction, a ratio of g to e may be 3.50% or less. As a result of intensive study, the applicant has found that usually, dogs tend to move their tails from side to side while cats tend to move their tails up and down. Therefore, in a state where the cat is in the diaper, the hole body portion is pulled in the longitudinal direction, and the diaper is likely to be displaced in the longitudinal direction. At this time, because the ratio of the length of the hole body portion in the longitudinal direction to the movable range is low, the amount of displacement of the diaper in the longitudinal direction caused by the hole body portion can be reduced.

According to one or more embodiments, a tail hole having a hole body portion through which the cat's tail is capable of being inserted and a notch portion that increases the dimension of the hole body portion by communicating with the hole body portion may be formed in the body portion, the fastening tape may be arranged in the stomach-side region, a target portion to which the fastening tape is to be fastened may be provided in the back-side region, and in a case where e represents a distance between the stomach-side edge and the target portion in the longitudinal direction and h represents a maximum length of the tail hole in the longitudinal direction, a ratio of h to e may be 5.5% or less. According to one or more embodiments, even in a case where the dimension of the tail hole (the hole body portion) is increased by the notch portion, the ratio of the length of the tail hole in the longitudinal direction to the movable range is low, which makes it possible to reduce the amount of displacement of the diaper in the longitudinal direction by the tail hole.

According to one or more embodiments, a tail hole having a hole body portion through which the cat's tail is capable of being inserted be provided in the body portion may, and a ratio of a maximum length of the hole body portion in the lateral direction to a maximum length of the absorbent core in the lateral direction may be 35% or more. When putting a diaper on a cat, a user inserts the cat's tail into the tail hole. As a result, the tail hole can be pulled in the lateral direction by the tail, and the absorbent core can be pulled in the lateral direction. As a result, the wrinkled absorbent core can be made flat, which makes it easy to secure the length of the absorbent core in the lateral direction while the diaper is being worn. The ratio of the maximum length of the hole body portion in the lateral direction to the maximum length of the absorbent core in the lateral direction is high. Therefore, the force of widening the absorbent core via the hole body portion is more easily transmitted to the entire absorbent core in the lateral direction. Accordingly, it is unlikely that the fit of the diaper will deteriorate due to the deformation of the absorbent core, the leakage of body fluid can be suppressed, and the cat in the diaper can easily move its legs all the times.

According to one or more embodiments, the tail hole may be arranged away from the back outer end edge positioned on the back side of the absorbent core, toward the back side. Because the tail hole is provided in a region that does not overlap with the absorbent core, the force of pulling the tail hole in the lateral direction by the tail is unlikely to be affected by the stiffness of the absorbent core. Accordingly, the effect of suppressing wrinkling of the absorbent core by using the tail is more easily obtained.

According to one or more embodiments, the absorbent core may have a constricted portion that curves inward in the lateral direction, at least a part of a stomach-side edge extending to the stomach side from an inner edge (or an innermost edge) of the constricted portion in the lateral direction may extend on the inner side in the lateral direction toward the inner edge from the stomach side, and the longitudinal edge of each of the leg opening portions may extend on the outer side in the lateral direction toward the back side from the stomach side. At the inner edge of the constricted portion, the absorbent core is short in the lateral direction. Therefore, it is easy to fit the absorbent core to portions where the length of both legs of the cat is small in the lateral direction. In addition, the length of the absorbent core in the lateral direction increases toward the stomach side from the inner edge of the constricted portion. Therefore, the length of the absorbent core in the lateral direction can be reduced at the inner edge of the constricted portion, and the area of the absorbent core on the stomach side can be secured. Furthermore, the longitudinal edge of the leg opening portions extends on the inner side in the lateral direction toward the stomach side from the back side, and inclines away from the outer edge of the absorbent core in an opposite direction. Therefore, the leg opening portions long in the lateral direction can be provided in a portion where the absorbent core is short in the lateral direction, the entire diaper can keep on wrapping around the cat's waist, and leakage or displacement can be suppressed.

(2) Configuration of Cat Diaper

Hereinafter, a cat diaper according to one or more embodiments will be described with reference to the drawings. It should be noted that, in the following description of the drawings, identical or similar portions will be given identical or similar reference signs. Here, the drawings are schematic views, and attention needs to be paid to the fact that the ratios between individual dimensions and the like are different from actual ones. Therefore, specific dimensions and the like need to be determined with reference to the following description. In addition, there may be a portion where the relationship or ratio between dimensions varies between drawings.

Figure 2:
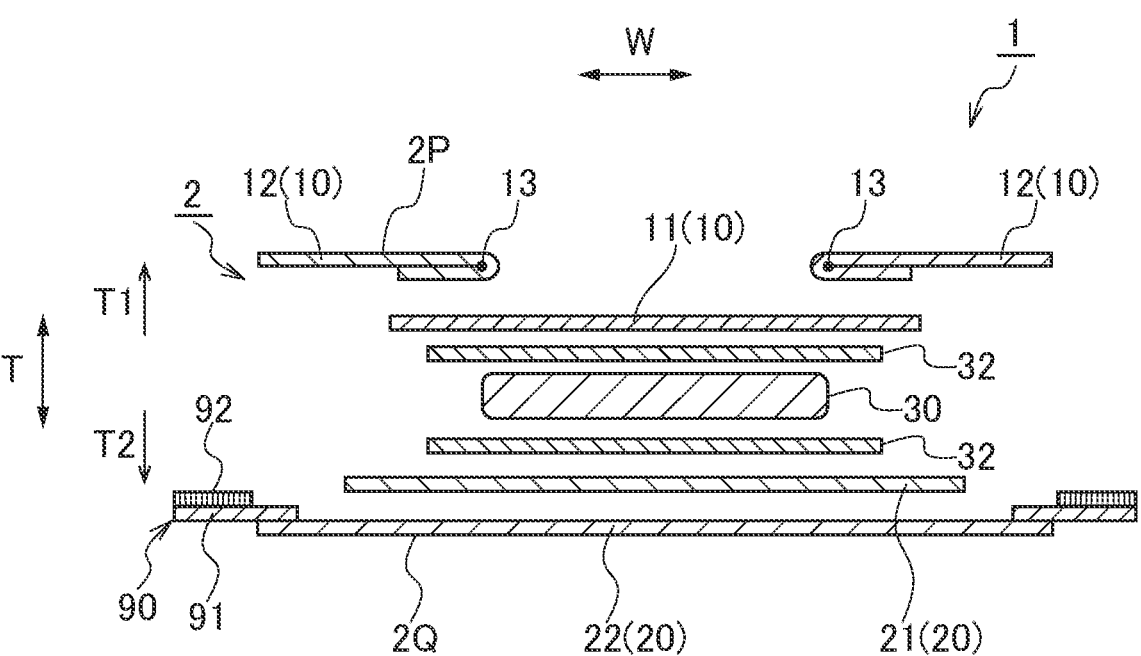
FIG. 2 is a schematic cross-sectional view of the cat diaper taken along a line A-A shown in FIG. 1.
Figure 3:
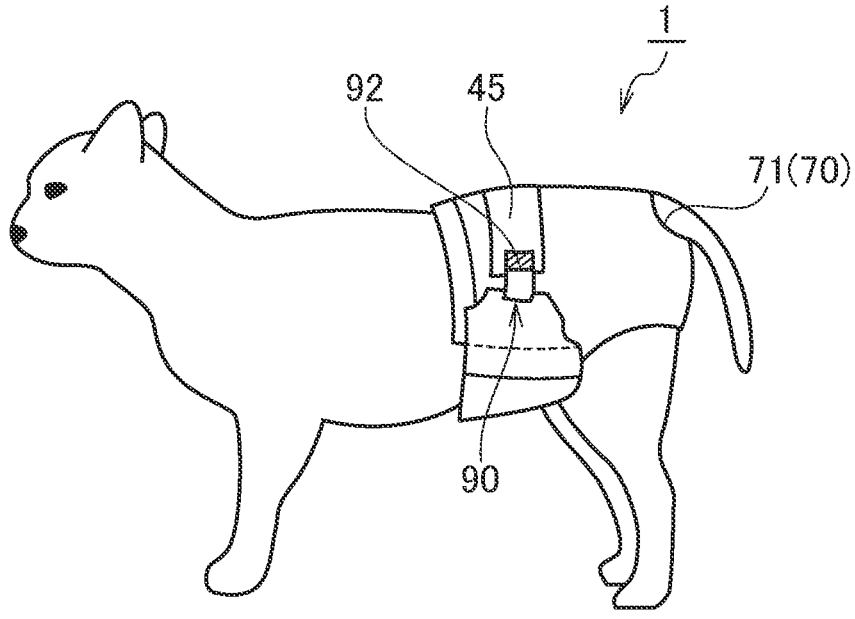
FIG. 3 is a view schematically showing a cat diaper according to one or more embodiments that is worn.

FIG. 1 is a plan view of a cat diaper according to one or more embodiments, seen from a top surface side T1 . FIG. 2 is a schematic cross-sectional view of the cat diaper taken along a line A-A shown in FIG. 1. FIG. 1 and FIG. 2 show a cat diaper 1 in a stretched state in which the diaper is stretched until no wrinkles are formed. In the cross-sectional view shown in FIG. 2, for the convenience of description, members are spaced apart in a thickness direction T. However, in an actual product, the members are in contact with each other the thickness direction T. FIG. 3 is a view schematically showing the cat diaper worn by a cat.

The cat diaper 1 has a lateral direction W arranged along a waistline direction of a cat, a longitudinal direction Z orthogonal to the lateral direction W, and a thickness direction T orthogonal to the lateral direction W and the longitudinal direction Z. The longitudinal direction Z extends in a direction connecting the stomach side and the back side of a cat. The thickness direction T extends to a top surface side T1 that comes into contact with a cat when the cat is in the diaper and a back surface side T2 that is exposed to the outer side when the cat is in the diaper. As shown in FIG. 3, the cat diaper of one or more embodiments is put on so as to cover the region ranging from the stomach side to back side of the cat through the crotch of the cat.

The cat diaper 1 may have a body portion 2 and a fastening tape 90. The cat diaper 1 may have a first end portion 61 of the body that is one end portion in the lateral direction W, a second end portion 62 of the body that is the other end portion in the lateral direction W, a third end portion 63 of the body that is one end portion in the longitudinal direction Z, and a fourth end portion 64 of the body that is the other end portion in the longitudinal direction Z. The fastening tape 90 is joined to the first end portion 61 of the body and the second end portion 62 of the body. The third end portion 63 of the body is arranged on the stomach side of the cat in the diaper. The fourth end portion 64 of the body faces the third end portion 63 of the body and is arranged on the back side of the cat in the diaper. In one or more embodiments of the present invention, an end portion is a portion that occupies a certain area including end edges. The first end portion 61 of the body is a portion that extends in the inner side in the lateral direction W from a first end edge 61E that is one end edge of the body portion 2 in the lateral direction W. Likewise, the second end portion 62 of the body is a portion that extends in the inner side in the lateral direction W from a second end edge 62E that is the other end edge of the body portion 2 in the lateral direction W. The first end portion of the body and the second end portion 62 of the body may be regions between end edges of the body portion 2 in the lateral direction W and end edges of the absorbent core 30 in the lateral direction W. The third end portion 63 of the body is a portion that extends on the inner side in the longitudinal direction Z from a third end edge 63E that is one end edge of the body portion 2 in the longitudinal direction Z. Likewise, the fourth end portion 64 of the body is a portion that extends on the inner side in the longitudinal direction Z from a fourth end edge 64E that is the other end edge of the body portion 2 in the longitudinal direction Z. The third end portion 63 of the body and the fourth end portion 64 of the body may be regions between end edges of the body portion 2 in the longitudinal direction Z and end edges of the absorbent core 30 in the longitudinal direction Z. The fourth end portion 64 of the body may be a region between an end edge of the body portion 2 in the longitudinal direction Z and an end edge of the absorbent core 30 in the longitudinal direction Z, or may be a region between an end edge of the body portion 2 in the longitudinal direction Z and a tail hole 70 comprising a hole body portion 71 and a notch portion 72 that will be described later.

The body portion 2 straddles a stomach-side region S1 that is brought into contact with the stomach side of a cat, a back-side region S2 that is brought into contact with the back side of the cat, and a crotch region S3 that is brought into contact with the crotch of the cat. The stomach-side region S1 is a region that includes the third end portion 63 of the body. The fastening tape 90 is arranged in the stomach-side region S1. The back-side region S2 is a region that includes the fourth end portion 64 of the body. The crotch region S3 is a region between the stomach-side region S1 and the back-side region S2. The crotch region S3 may be a region where a leg opening portion 5 is formed. The leg opening portion 5 is a region arranged around the cat's leg, and curves inward in the lateral direction W from the outer edge of the body portion 2. The outer edge of the body portion 2 is configured with the first end edge 61E and the second end edge 62E.

The body portion 2 has at least the top-surface sheet 10, the back-surface sheet 20, and the absorbent core 30. The top-surface sheet 10 is arranged on an inner surface 2P of the body portion 2 that is brought into contact with a cat. The top-surface sheet 10 has liquid permeability that enables a body fluid to permeate toward the absorbent core 30. The top-surface sheet 10 may have a center sheet 11 that is positioned at the center in the longitudinal direction Z and covers the absorbent core 30, and side sheets 12 that cover two side portions of the center sheet 11 in the lateral direction W. As shown in FIG. 2, the side sheets 12 may be folded. Specifically, the side sheets 12 are folded back toward the back surface side T2 at the inner edge of the side sheets 12 in the lateral direction W. Side stretchable members 13 being stretched in the longitudinal direction Z may be arranged between the folded side sheets 12. The side stretchable member 13 may constitute a leak-proof gather 15 that rises up toward the cat. The leak-proof gather 15 is a rising gather positioned closer to the skin side than the absorbent core 30 and has a rising portion 16 and a fixed portion 17. The rising portion 16 is a portion where the side sheet 12 is not fixed to the center sheet 11. This portion can rise up by the contraction of the side stretchable member 13. In a portion where the side sheet 12 is fixed to the center sheet 11, a portion positioned away from the rising portion 16 toward the outer side in the lateral direction W is the fixed portion 17. The leak-proof gather 15 is a portion where the side sheet 12 is fixed to the center sheet 11, and may have a second fixed portion 18 positioned away from the rising portion 16 toward the outer side in the longitudinal direction Z. The rising portion 16 can rise up toward the cat from the fixed portion 17 and the second fixed portion 18 as a base point.

The absorbent core 30 is arranged between the top-surface sheet 10 and the back-surface sheet 20. The absorbent core 30 is formed by laminating absorbent materials such as pulp. As shown in FIG. 2, a core wrap 32 that covers the absorbent core 30 may be provided. The absorbent core 30 is arranged away from two end edges of the body portion 2 toward the inner side in the lateral direction W. That is, the length of the absorbent core 30 in the lateral direction W is smaller than the length of the body portion 2 in the lateral direction W. The absorbent core 30 is arranged at the center of the body portion 2 in the lateral direction W, and is not provided on the outer side portion of the body portion 2 in the lateral direction W. The absorbent core 30 may be arranged away from two end edges of the body portion 2 toward the inner side in the longitudinal direction Z. That is, the length of the absorbent core 30 in the longitudinal direction Z may be smaller than the length of the body portion 2 in the longi-tudinal direction Z. The absorbent core 30 may be arranged at the center of the body portion 2 in the longitudinal direction Z, and may not be provided in the outer side portion of the body portion 2 in the longitudinal direction Z. The absorbent core 30 may be arranged straddling at least the crotch region S3 and the stomach-side region S1 and may not be arranged in the back-side region S2. A center CZ30 of the absorbent core 30 in the longitudinal direction may be positioned away from the center of the diaper in the longitudinal direction toward the stomach side. The absorbent core 30 may be spaced apart from the tail hole 70, which will be described later, in the longitudinal direction Z, and may be at a position closer to the stomach side than the tail hole 70. The absorbent core 30 will be specifically described later.

The back-surface sheet 20 is arranged on an outer surface 2Q of the body portion 2 that is positioned on the outer side while the diaper is being worn. The back-surface sheet 20 may have a liquid-impermeable back-surface film 21 and a back-surface nonwoven fabric 22 positioned on a side closer to the back surface than the back-surface film 21. It should be noted that, in a modified example, the back-surface sheet may have a liquid-impermeable back-surface film and a back-surface nonwoven fabric positioned on a side closer to the inner surface than the back-surface film 21. The length of the back-surface film 21 in the lateral direction W may be smaller than the length of the back-surface nonwoven fabric 22 in the lateral direction W. That is, the back-surface nonwoven fabric 22 may extend further toward two sides in the lateral direction W than the back-surface film 21.

In the third end portion 63 of the body which is one end portion of the body portion 2 in the longitudinal direction Z, the fastening tape 90 extends further toward both outer sides in the lateral direction W than the body portion 2. More specifically, in the third end portion 63 of the body, the fastening tape 90 extends further toward the outer side in the lateral direction W than the first end edge 61E and the second end edge 62E of the body portion 2. The fastening tape 90 joins the stomach-side region S1 and the back-side region S2. The fastening tape 90 may have a base sheet 91 that is joined to the body portion 2, and a joining portion 92 that is provided on the base sheet 91 and capable of being joined to the outer surface 2Q of the body portion 2. The joining portion 92 is arranged on a surface of the fastening tape 90 that faces the top surface side T1. The joining portion 92 may be a mechanical fastener and is configured to be joinable to a target portion 45 provided on the outer surface 2Q of the body portion 2. At least a part of the target portion 45 may be provided in the back-side region S2. The target portion 45 of one or more embodiments straddles the back-side region S2 and the crotch region S3. It should be noted that, in a modified example, the body portion 2 may not include the target portion 45, and the joining portion 92 may be configured to be joined to the back-surface sheet 20 of the body portion 2 on the outer surface 2Q side. In a modified example, the joining portion may extend further toward two outer sides in the lateral direction W than the body portion 2 in the fourth end portion 64 of the body.

The body portion 2 of the cat diaper 1 may be provided with the tail hole 70. The tail hole 70 may have the hole body portion 71 through which the tail of a cat is capable of being inserted. When the diaper having the tail hole 70 is worn so that the buttocks and back of the cat are covered with the fourth end portion 64 of the body, the cat's tail may be inserted into the hole body portion 71 of the tail hole 70. The hole body portion 71 may be a semicircular notch. The hole body portion 71 may be a continuous notch or may have a configuration, such as a perforation, making it possible to tear off (or rip up) the top-surface sheet 10 and the back-surface sheet 20. The tail hole 70 may have the notch portion 72 that increases the dimension of the hole body portion 71 by communicating with the hole body portion 71. In the example illustrated in FIG. 1, the tail hole 70 comprise four notch portions 72 on both sides of and below the hole body portion 71. The notch portion 72 may have a configuration, such as a perforation, making it possible to tear off the top-surface sheet 10 and the back-surface sheet 20 and communicate the notch portion 72 to the hole body portion 71. The dimension of the hole body portion 71 can be adjusted according to the type and the growth process of a cat. Two notch portions of one or more embodiments are provided on each of the left and right sides of the center of the tail hole 70 in the lateral direction W. In a modified example, one notch portion 72 may be provided on each of the left and right sides of the center of the tail hole 70 in the lateral direction W, or a configuration may be adopted in which two or more notch portions 72 may be provided so that the dimension of the tail hole 70 can be adjusted in multiple stages. The hole body portion 71 and the notch portion 72 may be portions where the top-surface sheet 10 and the back-surface sheet 20 are cut.

When the cat diaper 1 is put on a cat, the third end portion 63 of the body (the end portion on the side provided with the joining portion 92) is brought into contact with the cat's stomach. At this time, the fourth end portion 64 of the body is passed between two legs of the cat and extended toward the back of the cat. Then, the center of the body portion 2 in the longitudinal direction Z is brought into contact with the cat's urination opening, and at the same time, the cat's tail is slid through the tail hole 70 toward the back surface side T2 of the diaper. The buttocks and back of the cat are covered with the fourth end portion 64 of the body. Next, the joining portion 92 is pulled toward the back of the cat, and the joining portion 92 is fastened to the outer surface of the target portion 45 of the fourth end portion 64 of the body positioned on the back side. In this way, the cat diaper 1 can be put on so as to cover the stomach, back, and crotch of the cat as shown in FIG. 3. That is, the cat diaper 1 is worn so as to cover the region ranging from the stomach side to back side of the cat through the crotch of the cat.

The pet diaper of the conventional technique (for example, Japanese Patent Application Publication No. 2017-131160) is configured so that the diaper can be put on both the dogs and cats. As a result of extensive investigation, the applicant has found that there is a big difference in the shape of portions around the leg between cats and dogs. More specifically, dogs have relatively little flesh around the bone in the vicinity of the groin. Furthermore, in a state where a dog stands on four legs, the dog's legs are relatively straight although slightly bent at the joints. In contrast, compared to dogs, cats have more flesh around the bone in the vicinity of the groin. In addition, in a state where the cat stands on four legs, the cat's joints are bent much. Because cats have much flesh around the groin and their joints of the groin are bent as described above, fitting a diaper to the groin is harder in cats than in dogs in some cases. In a case where the diaper does not fit the groin, sometimes the diaper is displaced or detached while being worn.

Figure 4A:
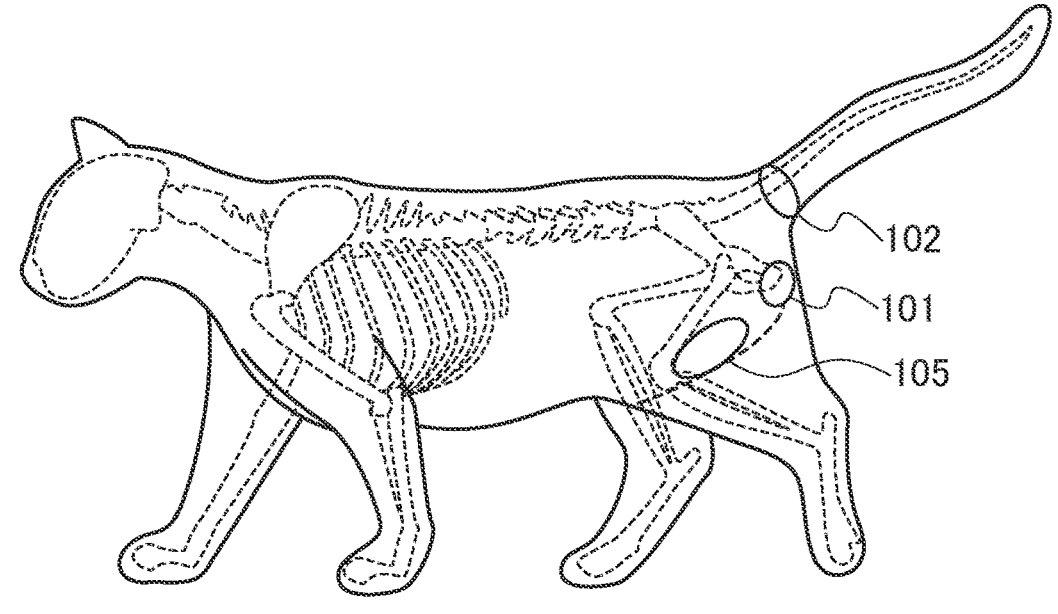
FIGS. 4A-4B are views each schematically showing the body shapes of a cat and a dog.
Figure 4B:
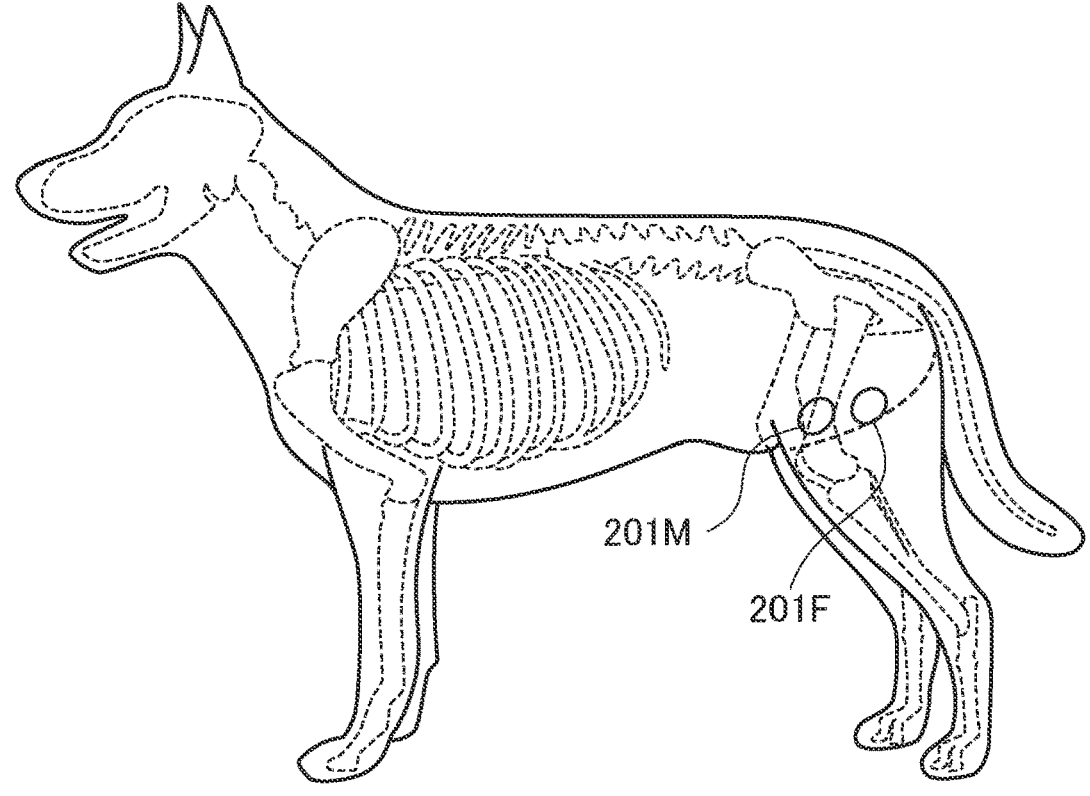

The diaper of one or more embodiments is configured to fit around the cat's leg so as to make it possible to inhibit the diaper from being displaced while being worn. Next, a configuration for making it easier to fit the diaper around the cat's leg will be specifically described. FIGS. 4A-4B are views each schematically showing the body shapes of a cat and a dog. FIG. 4A shows the body shape of a cat, and FIG. 4B shows the body shape of a dog. As shown in FIG. 1, the leg opening portion 5 may have a stomach-side edge 51 that extends to the inner side in the lateral direction W from an outer edge 2E of the body portion 2 on the stomach side, a back-side edge 52 that extends to the inner side in the lateral direction W from the outer edge 2E of the body portion 2 on the back side, and a longitudinal edge 53 that connects the stomach-side edge 51 and the back-side edge 52 and extends in the longitudinal direction Z. In a case where the longitudinal edge 53 is in the form of straight line and the stomach-side edge 51 and the back-side edge 52 are in the form of a curve, the boundary between the stomach-side edge 51 and the longitudinal edge 53 may be a boundary between the straight line and the curve. Furthermore, in a case where all of the stomach-side edge 51, the back-side edge 52, and the longitudinal edge 53 are in the form of a curve, a site where the curvature changes may be the boundary. In a case where there is a plurality of boundaries where the curvature changes, the boundaries may be set by adopting the portion that extends while forming an angle of 45° or less with the lateral direction W as the stomach-side edge 51 and the back-side edge 52 and adopting a portion that extends while forming an angle of less than 45° with the longitudinal direction Z as the longitudinal edge 53. In a case where the leg opening portion is in the shape of an arc having a constant radius of curvature, the intersection point between a virtual line that passes through the center of the radius of curvature of the arc and extends in the lateral direction and the leg opening portion 5 may be adopted as the boundary between the stomach-side edge 51 and the longitudinal edge 53 or the boundary between the back-side edge 52 and the longitudinal edge 53. In a case where the leg opening portion 5 is in the shape of an elliptical arc having a variation of radius of curvature, the intersection point of a virtual line that passes through each of the centers of the radius of curvature and extends in the lateral direction and the leg opening portion 5 may be the boundary between the stomach-side edge 51 and the longitudinal edge 53 or the boundary between the back-side edge 52 and the longitudinal edge 53.

As shown in FIG. 1, in a case where a represents a length of the stomach-side edge 51 in the longitudinal direction Z and b represents a length of the stomach-side edge 51 in the lateral direction W, a<b may be satisfied. In other words, the length a of the stomach-side edge 51 in the longitudinal direction Z is the distance between the stomach-side end edge of the leg opening portion 5 and the longitudinal edge 53 in the longitudinal direction Z. Furthermore, in other words, the length b of the stomach-side edge 51 in the lateral direction W is the distance between the first end edge 61E and the stomach-side end edge of the longitudinal edge 53 in the lateral direction W. When the diaper is put on a cat, the stomach-side region S1 is brought into contact with the cat's stomach side, the crotch region S3 is brought into contact with the cat's crotch, and the back-side region S2 is brought into contact with the cat's back side. In this state, the fastening tape 90 is fastened to the stomach-side region S1 and the back-side region S2. As shown in FIG. 3, in a state where the cat is in the diaper, the leg opening portion 5 is arranged to surround the cat's back leg, and the stomach-side edge 51 of the leg opening portion 5 comes into contact with the stomach-side surface of the cat's back leg. The length b of the stomach-side edge 51 in the lateral direction W is greater than the length a of the stomach-side edge 51 in the longitudinal direction Z. Therefore, when the leg opening portion 5 is fitted around the leg, a region can be secured which extends in the lateral direction W in a range short in the longitudinal direction Z. For example, in a case where a=b, because the length of the stomach-side edge 51 in the longitudinal direction Z is the same as the length thereof in the lateral direction W, the leg opening portion gently tightens the leg along the lateral direction in a range short in the longitudinal direction Z. Therefore, the diaper is likely to loosely fit around the leg.

As a result of extensive investigation, the applicant has found that there is a big difference in the shape of portions around the leg between cats and dogs as shown in FIGS. 4A-4B. More specifically, dogs have relatively little flesh around the bone in the vicinity of the groin. Furthermore, in a state where a dog stands on four legs, the dog's legs are relatively straight although slightly bent at the joints. In contrast, compared to dogs, cats have more flesh around the bone in the vicinity of the groin. In addition, in a state where the cat stands on four legs, the cat's joints are bent much. Because cats have much flesh around the groin and their joints of the groin are bent as described above, fitting a diaper to the groin is harder in cats than in dogs in some cases. In a case where the diaper does not fit the groin, sometimes the diaper is displaced or detached while being worn. However, in a case where a<b is satisfied, the leg opening portion tightens some parts of the leg toward the inner side in the lateral direction W within a range short in the longitudinal direction Z, which makes it easy to tightly fit the diaper around the leg. By tightly fitting the diaper around the legs, even for a cat which has relatively much flesh or has bent joints and thus not easy to tightly fit the diaper around the legs, a user can easily tightly fit the diaper around the legs without paying special attention, and the inconvenient condition in that the diaper is detached while being worn can be suppressed.

In a case where c represents a distance between the fastening tape 90 and the longitudinal edge 53 in the longitudinal direction Z, and b represents a length of the stomach-side edge 51 in the lateral direction W, c<b may be satisfied. The distance c between the fastening tape 90 and the longitudinal edge 53 in the longitudinal direction Z is in other words a distance between the boundary between the stomach-side edge 51 and the longitudinal edge 53 and the back-side end edge of the fastening tape 90 in the longitudinal direction Z. When the diaper is put on a cat, the fastening tape 90 is pulled in the lateral direction and joined to the target portion 45 or the like. At this time, the stomach-side edge 51 of the leg opening portion 5 is pulled in the lateral direction W, and a line that starts from the portion between both the back legs, passes through the back legs, and extends to the back side is configured with a line which connects the longitudinal edge 53 and the fastening tape 90 and extends in the longitudinal direction Z. Because the distance c is shorter than the length b of the stomach-side edge 51 in the lateral direction W, when the leg opening portion 5 is fitted around the leg, a region can be secured which extends in the lateral direction W within a range short in the longitudinal direction Z. Because the leg opening portion tightens some parts of the leg in the lateral direction within a range short in the longitudinal direction Z, it is easy to tightly fit the diaper around the leg. Tightly fitting the leg opening portions around the legs makes it possible to suppress the inconvenient condition in that the diaper is detached while being worn.

In a case where d represents a length of the body portion 2 in the longitudinal direction Z, a ratio of the length a of the stomach-side edge 51 in the longitudinal direction Z to d may be 10% or less. The length d of the body portion 2 in the longitudinal direction Z is in other words the distance between the third end edge 63E and the fourth end edge 64E in the longitudinal direction Z. The length of the body portion 2 in the longitudinal direction Z may be the total length of the cat diaper 1 in the longitudinal direction Z. Because the ratio of the length a of the stomach-side edge 51 in the longitudinal direction to the total length of the body portion 2 is low, the diaper can be inhibited from deviating from around the leg in the longitudinal direction Z. As a result, the inconvenient condition in that the diaper is detached while being worn due to the increase in the amount of displacement in the longitudinal direction Z or the diaper hinders the cat from moving its legs back and forth can be suppressed.

In a case where e represents a distance between the stomach-side edge 51 and the target portion 45 in the longitudinal direction, a ratio of e to the length d of the body portion 2 in the longitudinal direction Z may be 60% or more. The distance between the stomach-side edge 51 and the target portion 45 in the longitudinal direction is in other words the distance between the boundary between the stomach-side edge 51 and the longitudinal edge 53 and the target portion 45 in the longitudinal direction. The region between the stomach-side edge 51 and the target portion 45 in the longitudinal direction Z is a region that covers the body from the stomach side to the back side and is deformed in accordance with the body movement or the stretching and contraction of the skin in a state where the fastening tape 90 is fastened to the target portion 45 or the like. Because the ratio of the length e to the total length of the body portion 2 is high, a wide region deformed in accordance with the cat's movement can be secured. In addition, as a result of extensive investigation, the applicant has found that there is a big difference in the normal way of body movement between cats and dogs. Specifically, it has been found that, in many cases, while dogs tend to perform movement in a planar direction, such as running on the ground, cats tend to perform movement in a vertical direction, such as jumping up and down, unlike dogs. When trying to move its body in a vertical direction, a cat bends back legs and then instantly stretches them, or stretches the stomach or back that has been pulled in or hunched, as soon as it bends and stretches legs. Therefore, the skin around the stomach, the buttocks, and the legs are likely to stretch and contract much. Securing the length e makes it possible to cause the diaper to conform to the body movement in the vertical direction and to inhibit the diaper from being displaced by accident.

In a case where f represents a distance between the back-side end edge of the tail hole 70 and the target portion 45 in the longitudinal direction Z, a ratio of f to the length d of the body portion 2 in the longitudinal direction Z may be 20% or more. The distance f between the back-side end edge of the tail hole 70 and the target portion 45 in the longitudinal direction Z is the length of a region that covers a region from the tail hole 70 to the back side and is deformed in accordance with the body movement or the stretching and contraction of the skin on the back side in a state where the fastening tape 90 is fastened to the target portion 45. Unlike dogs, cats often take postures such as stretching with arching back, seating with arching back, or curling into a ball. In a case where cats take a posture of curling into a ball or a posture of stretching back, the back moves much or the skin on the back stretches or contracts much. Because the ratio of the length f to the total length of the body portion 2 is high, a wide region that is deformed in accordance with the cat's movement can be secured on the back side, which allows the diaper to conform to the movement of the back and makes it possible to inhibit the diaper from being displaced by accident. The distance f between the tail hole 70 (hole body portion 71+notch portion 72) and the target portion 45 in the longitudinal direction Z is not less than 20% of the length d of the body portion 2 in the longitudinal direction Z in one or more embodiments.

The distance f between the tail hole 70 (hole body portion 71+notch portion 72) and the target portion 45 in the longitudinal direction Z is the length of a region that deforms in accordance with the body movement or the stretching and contraction of the skin on the back side in a state where the tail hole opening widens by the notch portion 72. According to this configuration, even in a case where the dimension of the tail hole 70 is increased by the notch portion 72, a wide region that is deformed in accordance with the cat's movement can be secured on the back side, which allows the diaper to conform to the movement of the back side and makes it possible to inhibit the diaper from being displaced by accident.

In a case where g represents a maximum length of the hole body portion 71 in the longitudinal direction Z, a ratio of g to the distance e between the stomach-side edge 51 and the target portion 45 in the longitudinal direction Z may be 3.50% or less. In many cases, usually, dogs tend to move their tails from side to side while cats tend to move their tails up and down. Therefore, in a state where the cat is in the diaper, the hole body portion 71 is pulled in the longitudinal direction, and the diaper is likely to be displaced in the longitudinal direction Z. At this time, because the ratio of the length of the hole body portion 71 in the longitudinal direction to the length of the movable range is low, the amount of displacement of the diaper in the longitudinal direction Z by the hole body portion 71 can be reduced. Furthermore, in a case where h represents a maximum length of the tail hole in the longitudinal direction, a ratio of h to the distance e between the stomach-side edge 51 and the target portion 45 in the longitudinal direction Z may be 5.5% or less. The maximum length h of the tail hole 70 in the longitudinal direction Z is the maximum length of the tail hole 70 (hole body portion 71+notch portion 72) in the longitudinal direction Z. According to this configuration, in a case where the dimension of the tail hole 70 is increased by the notch portion 72, the ratio of the length of the tail hole 70 in the longitudinal direction to the movable range is low, which makes it possible to reduce the amount of displacement of the diaper in the longitudinal direction Z by the tail hole 70.

The ratio of the maximum length of the hole body portion 71 in the lateral direction W to the maximum length of the absorbent core 30 in the lateral direction W may be 35% or more. When a user inserts the cat's tail into the tail hole 70 for putting the diaper on the cat, the hole body portion 71 of the tail hole 70 can be pulled in the lateral direction W by the tail, and the force of hole body portion 71 in the lateral direction W is applied to the absorbent core 30. As a result, the absorbent core 30 widens in the lateral direction W, which makes it possible to suppress wrinkling of the absorbent core 30 and makes it easy to secure the length of the absorbent core 30 in the lateral direction W while the diaper is being worn. Especially, the ratio of the diameter of tail to the dimension of waistline is higher in cats than in dogs. Accordingly, it is easy to obtain the effect of suppressing wrinkling of the absorbent core 30 by using the tail. As a result, the wrinkled absorbent core 30 can be made flat, which makes it easy to secure the length of the absorbent core 30 in the lateral direction W while the diaper is being worn. In addition, the ratio of the maximum length of the hole body portion 71 in the lateral direction W to the maximum length of the absorbent core 30 in the lateral direction W is high. Therefore, the force of widening the absorbent core 30 by the hole body portion 71 is more easily transmitted to the entire absorbent core 30 in the lateral direction W. Accordingly, it is unlikely that the fit of the diaper will deteriorate due to the deformation of the absorbent core 30, the leakage of body fluid can be suppressed, and the cat in the diaper can easily move its legs all the times. The ratio of the maximum length of the tail hole 70 (hole body portion 71+notch portion 72) in the lateral direction W to the maximum length of the absorbent core 30 in the lateral direction W is more than 40% in one or more embodiments. According to this configuration, in a case where the dimension of the tail hole 70 is increased by the notch portion 72, the ratio of the maximum length of the hole body portion 71 in the lateral direction to the maximum length of the absorbent core 30 in the lateral direction is high. Therefore, the force of widening the absorbent core 30 by the tail hole 70 is more easily transmitted to the entire absorbent core 30 in the lateral direction W. The tail hole 70 may be arranged away from a back outer end edge R30, which is positioned on the back side of the absorbent core 30, toward the back side. Because the tail hole 70 is provided in a region that does not overlap with the absorbent core 30, the force of pulling the tail hole 70 in the lateral direction W by the tail is unlikely to be affected by the stiffness of the absorbent core 30. Accordingly, the effect of suppressing wrinkling of the absorbent core 30 by using the tail is more easily obtained.

Figure 5:
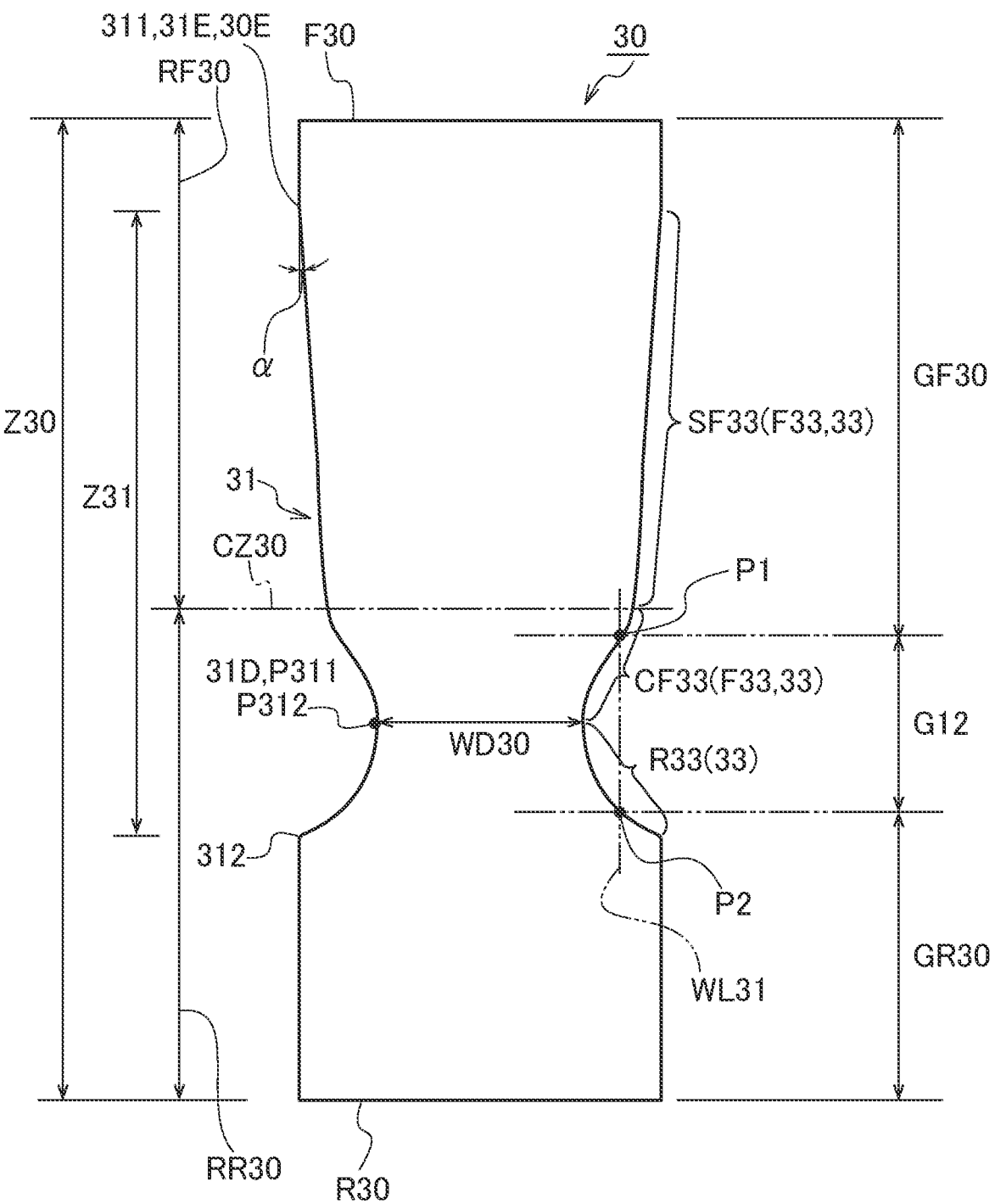
FIG. 5 is an enlarged plan view of an absorbent core according to one or more embodiments.

Next, the absorbent core 30 will be specifically described with reference to FIG. 5. FIG. 5 is an enlarged plan view of the absorbent core 30. The absorbent core 30 may have a constricted portion 31 that tapers toward the inner side in the lateral direction W. The constricted portion 31 is a portion that curves inward in the lateral direction W from an outer edge 30E of the absorbent core 30. An inner edge 31D of the constricted portion 31 is a portion of the constricted portion 31 that is positioned on the innermost side in the lateral direction. An outer edge 31E of the constricted portion 31 is a portion of the constricted portion 31 that is positioned on the outermost side in the lateral direction W, and may coincide with the outer edge 30E of the absorbent core 30. A stomach-side end edge P311 at the inner edge 31D of the constricted portion 31 in the lateral direction W may be positioned away from the center CZ30 of the absorbent core 30 in the longitudinal direction Z toward the back side. In a configuration in which the inner edge 31D of the constricted portion 31 does not extend in the longitudinal direction Z as in one or more embodiments, the stomach-side end edge P311 is a dot and coincides with a back-side end edge P312 at the inner edge 31D of the constricted portion 31. However, in a configuration in which the inner edge 31D of the constricted portion 31 extends in the longitudinal direction Z, the stomach-side end edge P311 is an edge positioned closest to the stomach side at the inner edge 31D extending in the longitudinal direction Z, and is spaced apart from the back-side end edge P312 in the longitudinal direction Z.

As shown in FIG. 3, in a state where a cat is in the diaper, the leg opening portion 5 is arranged to surround the cat's back leg, and the inner edge 31D of the constricted portion 31 of the absorbent core 30 is mainly fitted to a portion 105 (see FIGS. 4A-4B) where the leg width (space between both legs) is the smallest in a region from the back legs to the buttocks. At this time, in the case of conventional diaper for both dogs and cats, the stomach-side end edge P311 at the inner edge 31D of the constricted portion 31 is shifted and arranged toward the center CZ30 of the absorbent core 30 in the longitudinal direction Z or toward the stomach side. Therefore, the absorbent core 30 that extends to the stomach side from the position where the leg width is the smallest cannot secure a sufficient length in the longitudinal direction Z. As a result, in a case where the skin on the stomach stretches or contracts much as the cat moves in the vertical direction, the absorbent core 30 fails to keep conforming to the movement, which leads to the inconvenient condition in that the diaper is displaced or detached. Furthermore, in a case where the cat bends or stretches its back legs to move in the vertical direction, the absorbent core 30 that extends to the stomach side from the portion 105 where the leg width is the smallest is repeatedly deformed, which sometimes makes it difficult for the diaper to keep on covering the cat's body. As a result of observing the cat in the diaper, the applicant has found that the length of the absorbent core 30, which extends to the stomach side from the portion 105 where the leg width is the smallest, in the longitudinal direction Z corresponds to the length of the absorbent core 30, which extends to the stomach side from the stomach-side end edge P311, in the longitudinal direction. The stomach-side end edge P311 at the inner edge 31D of the constricted portion 31 in the lateral direction W is positioned away from the center CZ30 of the absorbent core in the longitudinal direction Z toward the back side. Therefore, the absorbent core 30 that extends to the stomach side from the portion 105 where the leg width is the smallest can be long enough in the longitudinal direction Z. Consequently, even in a case where the cat repeatedly moves its legs back and forth in moving in the vertical direction, the cat's body can be covered with the absorbent core 30. Furthermore, because the absorbent core 30 that extends to the stomach side from the portion 105 where the leg width is the smallest can be long enough in the longitudinal direction Z, even in a case where the skin on the stomach stretches and contracts much, the absorbent core can keep conforming to the movement, and the cat can keep on wearing the diaper.

A length Z31D (see FIG. 7) of the inner edge 31D of the constricted portion 31 in the longitudinal direction Z may be not more than 30% of a length Z30 of the absorbent core 30 in the longitudinal direction Z. In one or more embodiments, the inner edge 31D of the constricted portion 31 is in the shape of a dot. The length of the inner edge 31D in the longitudinal direction Z is not limited and close to 0. When the cat moves in the vertical direction, due to the impact of landing or the like or the stretching or contraction of the skin in the longitudinal direction, the diaper is easily displaced in the longitudinal direction Z. At this time, because the length of the inner edge 31D of the constricted portion 31 is 30% or less, in a state where the absorbent core is fitted to the portion 105 where the leg width is the smallest, the amount of displacement in the longitudinal direction Z is not more than 30% of the absorbent core. For example, even in a case where force is applied in the direction along which the diaper is displaced due to impact or the like, the cat's body can be kept covered with the diaper. The length Z31D of the inner edge 31D in the longitudinal direction Z may be not more than 40% of a length Z31 of the constricted portion 31 in the longitudinal direction Z. In the constricted portion 31, the ratio of the length of the inner edge 31D in the longitudinal direction Z is low, the amount of displacement of the diaper in the longitudinal direction Z can be limited.

The constricted portion 31 has a side edge 33 that connects a front end edge 311 positioned on the stomach side, a back end edge 312 positioned on the back side, and the inner edge 31D. The front end edge 311 is an edge of the constricted portion 31 closest to the stomach side, and the back end edge 312 is an edge of the constricted portion 31 closest to the back side. The side edge 33 has a stomach-side edge F33 that extends from the front end edge 311 to the inner edge 31D and a back-side edge R33 that extends from the back end edge 312 to the inner edge 31D. The stomach-side edge F33 and the back-side edge R33 may not be symmetrical about a lateral virtual line extending in the lateral direction W and may be asymmetrical about such a line. The stomach-side edge F33 has a portion SF33 that linearly extends to the back side from the front end edge 311 and a portion CF33 in the form of a curve that connects the linearly extending portion SF33 and the inner edge 31D. The linearly extending portion SF33 inclines away from the longitudinal direction Z at an angle α. The angle a is smaller than an angle of inclination at which the portion CF33 extending in the form of a curve inclines away from the longitudinal direction Z. Furthermore, at the stomach-side edge F33, the length of linearly extending portion SF33 in the longitudinal direction Z is smaller than the length of the portion CF33 extending in the form of a curve in the longitudinal direction Z. Therefore, the stomach-side edge F33 is gently curved in along the lateral direction W within a region taking up ½ or more of the constricted portion 31 in the longitudinal direction Z, and caved in some parts in the lateral direction W in a range of the constricted portion 31 short in the longitudinal direction Z. As a result, the displacement of the diaper around the cat's leg in the longitudinal direction Z can be further suppressed. The back-side edge R33 is in the form of a curve that extends to the inner edge 31D from the back end edge 312, and may not have a linearly extending portion.

The distance G12 between a first intersection point P1 where a virtual line WL31 passing through the center of the constricted portion 31 in the lateral direction W and extending in the longitudinal direction intersects with the stomach-side edge F33 and a second intersection point P2 where the virtual line WL31 intersects with the back-side edge R33 may be less than 40% of the length Z30 of the absorbent core 30 in the longitudinal direction Z. The distance G12 between the first intersection point P1 and the second intersection point P2 is the length of the constricted portion 31 in the longitudinal direction Z at the center of the constricted portion 31 in the lateral direction W, and is the length of a range in which the absorbent core 30 is likely to be displaced in the longitudinal direction Z without coming into close contact with the back leg. Because the distance G12 between the first intersection point P1 and the second intersection point P2 is less than 40% of the length Z30 of the absorbent core 30 in the longitudinal direction Z, the amount of displacement of the diaper in periphery of the beck leg in the longitudinal direction Z is likely to be limited to not more than 40% of the absorbent core 30. For example, even in a case where force that makes the diaper displaced in the longitudinal direction Z due to impact or the like acts, the cat's body can be kept covered with the diaper.

At least a part of the stomach-side edge F33 that extends toward the stomach side in the constricted portion 31 of the absorbent core 30 may extend on the outer side in the lateral direction W, toward the stomach side from the inner edge 31D. More specifically, within the stomach-side edge F33, each of the portion SF33 that linearly extends toward the back side from the front end edge 311 and the portion CF33 that extends in the form of a curve extends on the outer side in the lateral direction W, toward the stomach side from the inner edge 31D. In this way, the length of the absorbent core 30 in the lateral direction W is reduced at the inner edge 31D of the constricted portion 31, which makes it easy to fit the absorbent core 30 to a portion where the length of both legs of the cat is small in the lateral direction. Particularly, because the leg width is smaller in cats than in dogs, reducing the length of the absorbent core 30 in the lateral direction W makes it possible to more preferably fit the diaper to the cat's body shape. Furthermore, because the length of the absorbent core 30 in the lateral direction W increases toward the stomach side from the inner edge 31D of the constricted portion 31, the length of the absorbent core 30 in the lateral direction W can be reduced at the inner edge 31D of the constricted portion 31, and at the same time, the area of the absorbent core 30 on the stomach side can be secured. The longitudinal edge 53 of the leg opening portion 5 may extend on the outer side in the lateral direction W, toward the back side from the stomach side. The portion that extends on the outer side in the lateral direction W toward the back side from the stomach side straddles the region closer to the stomach side than the inner edge 31D and the region closer to the back side than the inner edge. The longitudinal edge 53 of the leg opening portion 5 extends on the inner side in the lateral direction W toward the stomach side from the back side, and inclines in the opposite direction of the outer edge of the absorbent core 30. Therefore, the leg opening portion 5 long in the lateral direction W can be provided in the portion where the absorbent core 30 is short in the lateral direction W, which enables the entire diaper to keep on wrapping up the cat's waist and makes it possible to suppress leakage or displacement.

The absorbent core 30 has a front outer end edge F30 positioned on the stomach side and the back outer end edge R30 positioned on the back side. The front outer end edge F30 is an edge of the absorbent core 30 that is closest to the stomach side, and the back outer end edge R30 is an edge of the absorbent core 30 that is closest to the stomach side. A distance GF30 between the front outer end edge F30 and the first intersection point P1 may be longer than a distance GR30 between the back outer end edge R30 and the second intersection point P2. The first intersection point P1 and the second intersection point P2 are positioned at the center of the constricted portion 31 in the lateral direction W, and are likely to come into contact with the center of the cat's back leg in the lateral direction W. The length of the absorbent core 30, which extends toward the stomach side from the center of the constricted portion 31 in the lateral direction W, in the longitudinal direction Z is greater than the length of the absorbent core 30, which extends toward the back side from the center of the constricted portion 31 in the lateral direction W, in the longitudinal direction Z. Because the absorbent core 30 that extends toward the stomach side from the back leg can be long enough in the longitudinal direction Z, even in a case where the skin on the stomach stretches and contracts much, the absorbent core 30 can keep conforming to the movement, which makes it easy for the cat to keep on wearing the diaper. Furthermore, in order for the absorbent core 30 extending toward the stomach side from the back leg to be long enough in the longitudinal direction Z, at least a part of the inner edge 31D of the constricted portion 31 may be positioned away from the center CZ30 of the absorbent core 30 in the longitudinal direction Z toward the stomach side.

The absorbent core 30 has a stomach-side region RF30 that is positioned away from the center CZ30 of the absorbent core 30 in the longitudinal direction Z toward the stomach side and a back-side region RR30 positioned away from the center CZ30 of the absorbent core 30 in the longitudinal direction Z toward the back side. The area of the stomach-side region RF30 may be larger than the area of the back-side region RR30. The urination opening 201F of a female dog is likely to come into contact with the back-side region RR30, and the urination opening 201M of a male dog is likely to come into contact with the stomach-side region RF30. In contrast, the urination opening 101 of both the male and female cats is likely to come into contact with the back-side region RR30. Increasing the area of the stomach-side region RF30 in a cat diaper makes it possible for the diaper to retain body fluid diffusing to the stomach-side region RF30 from the back-side region RR30. Drinking small amounts of water in general, cats are susceptible to urinary diseases. The cats with urinary diseases often show the symptoms of polydipsia and polyuria. The cats with polyuria have a higher tendency to pass urine that spreads in the stomach-side region RF30 of the absorbent core 30. Increasing the area of the stomach-side region RF30 makes it possible for the diaper to retain the body fluid diffusing to the stomach-side region RF30 from the back-side region RR30 even in a case where the cat has polyuria.

A length WD30 of the absorbent core 30 in the lateral direction W at the inner edge 31D of the constricted portion 31 may be not more than 80% of the maximum length of the absorbent core 30 in the lateral direction within the back-side region RR30. The length WD30 of the absorbent core 30 in the lateral direction W at the inner edge 31D of the constricted portion 31 is the distance between the left and right inner edges 31D. In one or more embodiments, the maximum length of the absorbent core 30 in the lateral direction within the back-side region RR30 is the distance between the outer edges 30E of the absorbent core 30. The difference between the maximum length of the absorbent core 30 in the lateral direction W within the back-side region RR30 and the length of the absorbent core 30 in the lateral direction W at the inner edge 31D of the constricted portion 31 can be made large. As described above, the urination opening 101 of both the male and female cats is likely to come into contact with the back-side region RR30. In the cat diaper, in a case where the maximum length of the absorbent core 30 in the lateral direction W within the back-side region RR30 is increased, the absorption capacity of the back-side region RR30 can secured. In addition, the distance between the urination opening 101 and the tail 102 is shorter in cats than in dogs, which makes it easier for the cat's body fluid to leak from the tail hole 70. Increasing the maximum length of the absorbent core 30 in the lateral direction W within the back-side region RR30 makes it possible to secure absorption capacity of the back-side region RR30 and to inhibit the body fluid from leaking from the tail hole 70. Furthermore, generally, the individual difference in body shape is smaller between cats than between dogs, and the leg width of the portion 105 where the leg width is the smallest is smaller in cats. Reducing the length WD30 of the absorbent core 30 in the lateral direction W at the inner edge 31D of the constricted portion 31 makes it possible to properly fit the diaper to the portion 105 where the leg width is the smallest.

As shown in FIG. 1, a maximum length M70 of the tail hole 70 in the lateral direction W may be equal to or greater than the length WD30 of the absorbent core 30 in the lateral direction W at the inner edge 31D of the constricted portion 31. In the tail hole 70 having the notch portion 72, a maximum length M30 of the tail hole 70 in the lateral direction W is the total length of a region consisting of the hole body portion 71 and the notch portion 72 in the lateral direction W. In one or more embodiments, the maximum length M30 is the distance between the outer edges of the notch portion 72 positioned on the outermost side in the lateral direction W. In a case where a user inserts the tail 102 into the tail hole 70 so as to put the diaper on the cat, the tail hole 70 can be pulled in the lateral direction W by the tail, and the force of stretching the tail hole in the lateral direction W is applied to the absorbent core 30. As a result, the absorbent core 30 widens in the lateral direction, which makes it possible to suppress the wrinkling of the absorbent core and makes it easy to secure the length of the absorbent core 30 in the lateral direction W while the diaper is being worn. Especially, the ratio of the diameter of tail to the dimension of waistline is higher in cats than in dogs. Accordingly, it is easy to obtain the effect of suppressing wrinkling of the absorbent core 30 by using the tail. Because the maximum length M70 of the tail hole 70 in the lateral direction W is equal to or greater than the length WD30 of the absorbent core 30 of the constricted portion 31 in the lateral direction W, in a case where the force of widening the absorbent core 30 acts on the entire tail hole 70 in the lateral direction W, the entire absorbent core 30 in the lateral direction W in the constricted portion 31 can widen. Furthermore, because the tail hole 70 extends to the outer side in the lateral direction from the inner edge 31D of the constricted portion 31, the absorbent core 30 can be pulled from the outer side in the lateral direction W, which makes it possible to further suppress wrinkling of the absorbent core 30.

The tail hole 70 may be arranged away from the back outer end edge R30, which is positioned on the back side of the absorbent core 30, toward the back side. That is, the tail hole 70 and the absorbent core 30 may be spaced apart in the longitudinal direction Z. Because the tail hole 70 is provided in a region that does not overlap with the absorbent core 30, the force of pulling the tail hole 70 in the lateral direction W by the tail is unlikely to be affected by the stiffness of the absorbent core 30. Accordingly, the effect of suppressing wrinkling of the absorbent core 30 by using the tail is more easily obtained.

The region that overlaps with the constricted portion 31 when seen in a plan view may be provided with an overlap portion R32 (see FIG. 1) where the core wraps 32 overlap with each other. The overlap portion R32 is a region where the absorbent core 30 is not arranged and the core wraps 32 come into contact with each other. The absorbent core 30 is not arranged in the constricted portion 31. In some cases, compared to the region where the absorbent core 30 is arranged, the constricted portion 31 is more unlikely to maintain stiffness. However, stacking and arranging the core wraps 32 on the overlap portion R32 makes it possible to increase the stiffness of the vicinity of the constricted portion 31. In this way, wrinkling of the constricted portion 31 of the absorbent core 30 can be suppressed, and the fit of the diaper can be maintained.

In a stretched state where the diaper is stretched, an inner edge 17D of the fixed portion 17 of the leak-proof gather 15 in the lateral direction W may be positioned away from the inner edge 31D of the constricted portion 31 toward the outer side in the lateral direction W. In the leak-proof gather 15, the rising portion 16 rises up from the fixed portion 17 as a base point, and sometimes the rising portion 16 and the entirety of the fixed portion 17 rise up from the absorbent core 30 as a base point due to the stiffness difference in the absorbent core 30. At this time, in the region where the constricted portion 31 is provided, the inner edge 17D of the fixed portion 17 is positioned away from the inner edge 31D of the constricted portion 31, which is the outer edge of the absorbent core 30, toward the outer side in the lateral direction W. Accordingly, the rising portion 16 and the entire fixed portion 17 rise up from the inner edge of the constricted portion 31 as a base point. In the region where the constricted portion 31 is provided, because the length of the absorbent core 30 in the lateral direction W is relatively small, there is a risk that the body fluid will be guided to the outer side of the absorbent core in the lateral direction.

However, because the rising portion 16 that rises up is high enough, leakage can be suppressed.

Figure 6:
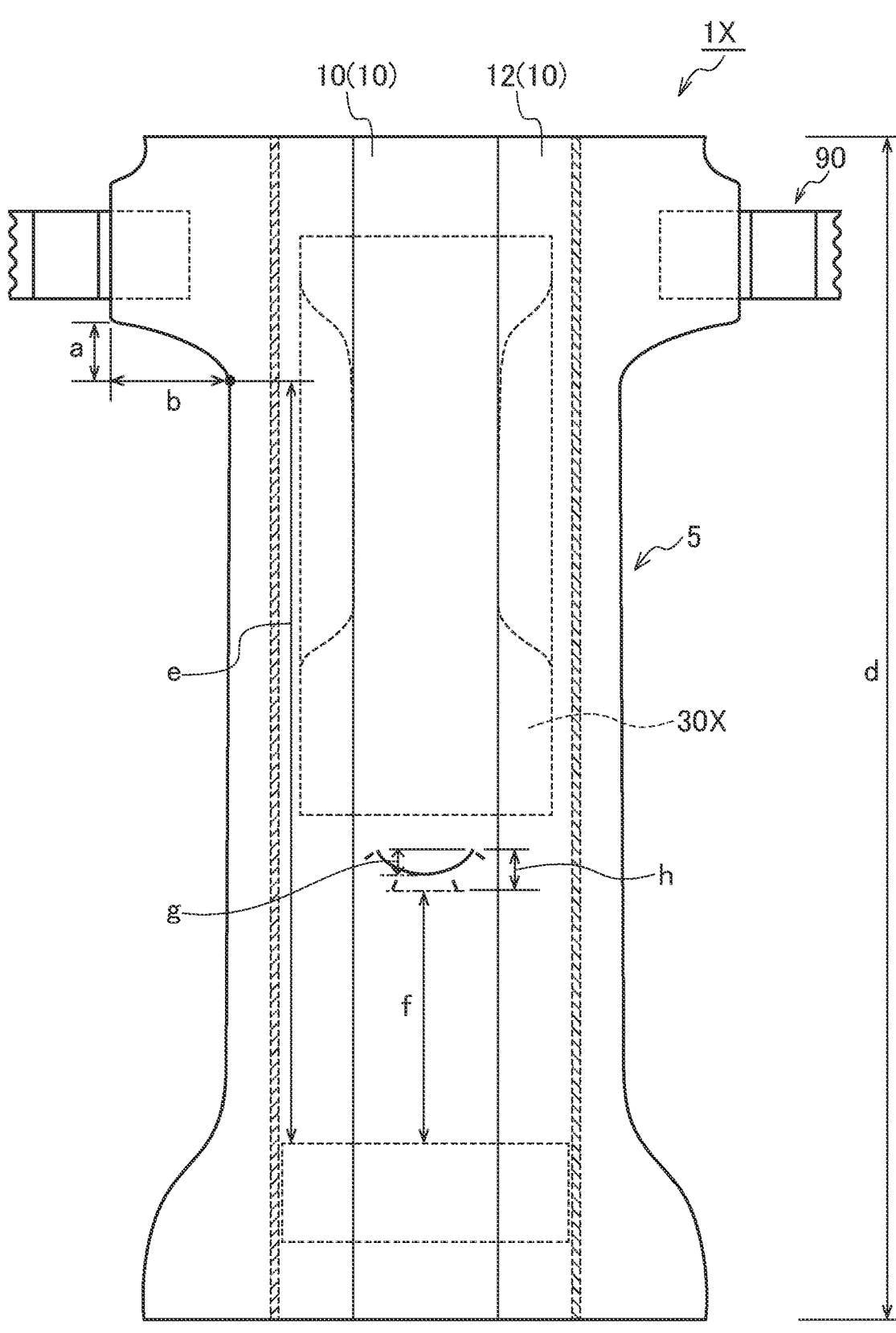
FIG. 6 is a plan view of a cat diaper according to one or more embodiments, seen from a skin surface side.
Figure 7:
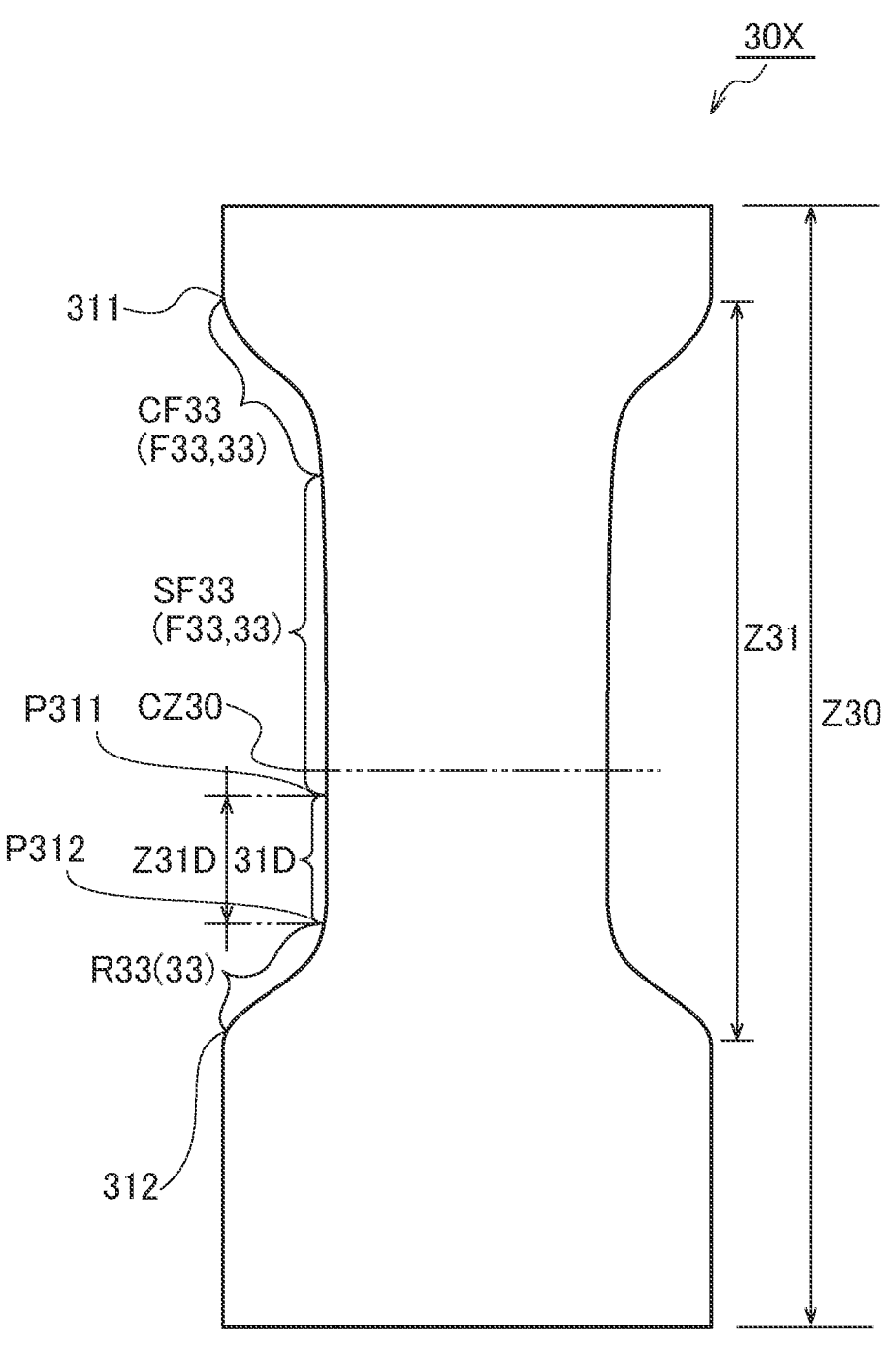
FIG. 7 is an enlarged plan view of an absorbent core according to a modified example.

Next, a cat diaper 1X according to a modified example will be described with reference to FIGS. 6-7. In the following description of the modified example, the same configurations as those in the above embodiments will be given the same reference signs and will not be described again. FIG. 6 is a plan view of the cat diaper 1X according to a modified example, seen from the skin surface side. FIG. 7 is a plan view of an absorbent core 30X according to the modified example. The inner edge 31D of the constricted portion 31 of the absorbent core 30X according to the modified example is provided in a certain range that extends in the longitudinal direction Z. The constricted portion 31 according to the modified example has the side edge 33 that connects the front end edge 311 positioned on the stomach side, the back end edge 312 positioned on the back side, and the inner edge 31D. The side edge 33 has a stomach-side edge F33 that extends from the front end edge 311 to the inner edge 31D and a back-side edge R33 that extends from the back end edge 312 to the inner edge 31D. The stomach-side edge F33 and the back-side edge R33 are not symmetrical about a lateral virtual line extending in the lateral direction W. The stomach-side edge F33 has the portion CF33 that linearly extends to the back side from the front end edge 311 and the portion CF33 in the form of a curve that connects the portion SF33 extending in the form of a curve and the inner edge 31D. The linearly extending portion SF33 inclines away from the longitudinal direction Z at an angle a. The angle a is smaller than an angle of inclination at which the portion CF33 extending in the form of a curve inclines away from the longitudinal direction Z. This angle is approximately close to 0° (5° or less). Furthermore, at the stomach-side edge F33, the length of linearly extending portion SF33 in the longitudinal direction Z is greater than the length of the portion CF33 extending in the form of a curve in the longitudinal direction Z. The back-side edge R33 is in the form of a curve that extends to the inner edge 31D from the back end edge 312, and may not have a linearly extending portion.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

INDUSTRIAL APPLICABILITY

A cat diaper that is not easily displaced while being worn can be provided.

REFERENCE SIGNS LIST

1, 1X: cat diaper
2: body portion
5: leg opening portion
51: stomach-side edge
52: back-side edge
53: longitudinal edge
10: top-surface sheet
15: leak-proof gather
16: rising portion
17: fixed portion
20: back-surface sheet
30, 30X: absorbent core F30: front outer end edge
R30: back outer end edge
31: constricted portion
311: front end edge
312: back end edge
70: tail hole
71: hole body portion
72: notch portion
90: fastening tape
RF30: stomach-side region
RR30: back-side region
S1: stomach-side region
S2: back-side region
S3: crotch region
T: thickness direction
W: lateral direction
Z: longitudinal direction

What is claimed is:

1. A cat diaper having a lateral direction along a waistline of a cat and a longitudinal direction orthogonal to the lateral direction, the cat diaper comprising:
  a body portion that:
    comprises an absorbent core, and
    has a stomach region, a crotch region, and a back region;
  leg opening portions that respectively correspond to legs of the cat; and
  a fastening tape that extends from each side of the body portion in the lateral direction, and joins the stomach region and the back region, wherein
  each of the leg opening portions has:
    a stomach-side opening edge that extends, on a stomach side of the cat diaper, to an inner side in the lateral direction from a lateral outer edge of the body portion,
    a back-side opening edge that extends, on a back side of the cat diaper, to an inner side in the lateral direction from the lateral outer edge of the body portion, and
    a longitudinal opening edge that connects the stomach-side opening edge and the back-side opening edge and extends in the longitudinal direction,
  $a<b$ is satisfied, where a represents a length of the stomach-side opening edge in the longitudinal direction and b represents a length of the stomach-side opening edge in the lateral direction,
  the body portion has a tail hole comprising a hole body through which a tail of the cat is inserted,
  the absorbent core has a constricted portion that curves inward in the lateral direction, and
  a maximum length of the tail hole in the lateral direction is equal to or larger than a width between innermost edges of the constricted portion in the lateral direction.

2. A cat diaper having a lateral direction along a waistline of a cat and a longitudinal direction orthogonal to the lateral direction, the cat diaper comprising:
  a body portion that:
    comprises an absorbent core, and
    has a stomach region, a crotch region, and a back region;
  leg opening portions that respectively correspond to legs of the cat; and
  a fastening tape that extends from each side of the body portion in the lateral direction, and joins the stomach region and the back region, wherein each of the leg opening portions has:
    a stomach-side opening edge that extends, on a stomach side of the cat diaper, to an inner side in the lateral direction from a lateral outer edge of the body portion,
    a back-side opening edge that extends, on a back side of the cat diaper, to an inner side in the lateral direction from the lateral outer edge of the body portion, and
    a longitudinal opening edge that connects the stomach-side opening edge and the back-side opening edge and extends in the longitudinal direction,
  $c<b$ is satisfied, where c represents a distance between the fastening tape and the longitudinal opening edge in the longitudinal direction and b represents a length of the stomach-side opening edge in the lateral direction,
  the absorbent core has:
    a stomach core region positioned between the center of the absorbent core in the longitudinal direction and a stomach side of the cat diaper, and
    a back core region positioned between the center of the absorbent core in the longitudinal direction and the back side, and
  an area of the stomach core region is larger than an area of the back core region, and
  the longitudinal opening edge of each of the leg opening portions extends outward in the lateral direction from the stomach side toward the back side.

3. The cat diaper according to claim 1, wherein a ratio of a to d is 10% or less, where d represents a length of the body portion in the longitudinal direction.

4. The cat diaper according to claim 1, wherein the fastening tape is disposed in the stomach region, the back region includes at least a part of a target portion to which the fastening tape is fastened, and a ratio of e to d is 60% or more, where e represents a distance between the stomach-side opening edge and the target portion in the longitudinal direction and d represents a length of the body portion in the longitudinal direction.

5. The cat diaper according to claim 1, wherein the fastening tape is disposed in the stomach region, the back region includes at least a part of a target portion to which the fastening tape is fastened, and a ratio of f to d is 20% or more, where f represents a distance between a back-side tail edge of the tail hole and the target portion in the longitudinal direction and d represents a length of the body portion in the longitudinal direction.

6. The cat diaper according to claim 1, wherein the fastening tape is disposed in the stomach region, the back region includes at least a part of a target portion to which the fastening tape is fastened, and a ratio of g to e is 3.50% or less, where e represents a distance between the stomach-side opening edge and the target portion in the longitudinal direction and g represents a maximum length of the hole body in the longitudinal direction.

7. The cat diaper according to claim 1, wherein the tail hole further comprises:
  a notch that increases a dimension of the hole body by communicating with the hole body,
  the fastening tape is disposed in the stomach region, the back region includes a target portion to which the fastening tape is fastened, and
  a ratio of h to e is 5.5% or less, where e represents a distance between the stomach-side opening edge and the target portion in the longitudinal direction and h represents a maximum length of the tail hole in the longitudinal direction.

8. The cat diaper according to claim 1, wherein a ratio of a maximum length of the hole body in the lateral direction to a maximum length of the absorbent core in the lateral direction is 35% or more.

9. The cat diaper according to claim 1, wherein the constricted portion has a stomach-side edge, at least a part of which extends to an inner side in the lateral direction toward the innermost edges from the stomach side, and the longitudinal opening edge of each of the leg opening portions extends to the outer side toward the back side from the stomach side.

* * * * *